(12) United States Patent
Telang et al.

(10) Patent No.: US 11,708,330 B2
(45) Date of Patent: *Jul. 25, 2023

(54) COMPOUNDS, COMPOSITIONS, METHODS FOR TREATING DISEASES, AND METHODS FOR PREPARING COMPOUNDS

(71) Applicant: UNIVERSITY OF LOUISVILLE RESEARCH FOUNDATION, INC., Louisville, KY (US)

(72) Inventors: Sucheta Telang, Louisville, KY (US); Jason Chesney, Louisville, KY (US); John O. Trent, Louisville, KY (US); Joseph A. Burlison, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/642,059

(22) PCT Filed: Aug. 30, 2018

(86) PCT No.: PCT/US2018/048660
§ 371 (c)(1),
(2) Date: Feb. 26, 2020

(87) PCT Pub. No.: WO2019/046497
PCT Pub. Date: Mar. 7, 2019

(65) Prior Publication Data
US 2020/0299241 A1    Sep. 24, 2020

Related U.S. Application Data

(60) Provisional application No. 62/552,716, filed on Aug. 31, 2017.

(51) Int. Cl.
*C07D 215/42* (2006.01)
*A61P 35/00* (2006.01)
*A61K 9/00* (2006.01)

(52) U.S. Cl.
CPC .......... *C07D 215/42* (2013.01); *A61P 35/00* (2018.01); *A61K 9/0019* (2013.01); *A61K 9/0053* (2013.01)

(58) Field of Classification Search
CPC .................................................. C07D 215/42
See application file for complete search history.

(56) References Cited

U.S. PATENT DOCUMENTS

| | | | |
|---|---|---|---|
| 4,035,367 A | 7/1977 | Simpson | |
| 7,759,392 B2 | 7/2010 | Soldato | |
| 3,088,385 A1 | 1/2012 | Chesney et al. | |
| 8,283,332 B2 | 10/2012 | Telang et al. | |
| 2010/0267815 A1 | 10/2010 | Telang et al. | |
| 2010/0273841 A1 | 10/2010 | Okuno et al. | |
| 2013/0289083 A1 | 10/2013 | Mautino et al. | |
| 2015/0376132 A1 | 12/2015 | Lee et al. | |

FOREIGN PATENT DOCUMENTS

| | | | |
|---|---|---|---|
| WO | 2014/134705 A1 | | 9/2014 |
| WO | 2015/040169 A1 | | 3/2015 |
| WO | WO 2015040424 | * | 3/2015 |
| WO | 2016/172499 A1 | | 10/2016 |

OTHER PUBLICATIONS

Dang. Cancer Discovery, 2012, 2, 304-307 (Year: 2012).*
Prichard. British Journal of Surgery, 2003, 90, 772-783 (Year: 2003).*
Black, Journal of Chemical Education, 1990, 67(2), 141-142 (Year: 1990).*
PCT/US2018/048660 ISR dated Nov. 12, 2018, 5 pages.
PCT/US2018/048660 Written Opinion dated Nov. 12, 2018, 5 pages.
CAS database RN 1329224-26-1, 1 page (2011).
Chenna et al., "Multiple sequence alignment with the Clustal series of programs" Nucleic Acids Res (2003) vol. 31, No. 13, pp. 3497-3500.
Chesney et al., "Fructose-2,6-bisphosphate synthesis by 6-phosphofructo-2-kinase/fructose-2,6-bisphosphatase 4 (PFKFB4) is required for the glycolytic response to hypoxia and tumor growth" Oncotarget (2014) vol. 5, No. 16, pp. 6670-6686.
Chesney et al., "Targeting the sugar metabolism of tumors with a first-in-class 6-phosphofructo-2-kinase (PFKFB4) inhibitor" Oncotarget (2015) vol. 6, No. 20, pp. 18001-18011.
Colosia et al., "Isolation of a cDNA clone for rat liver 6-phosphofructo 2-kinase/fructose 2,6-bisphosphatase" Biochem Biophys Res Commun (1987) vol. 143, No. 3, pp. 1092-1098.
El-Maghrabi et al., "Tissue distribution, immunoreactivity, and physical properties of 6-phosphofructo-2-kinase/fructose-2,6-bisphosphatase" Proc Natl Acad Sci USA (1986) vol. 83, No. 14, pp. 5005-5009.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study" Lancet Oncol (2015) vol. 16, No. 1, pp. 25-35.

(Continued)

*Primary Examiner* — Noble E Jarrell
(74) *Attorney, Agent, or Firm* — ALGM LLP; Harry J. Guttman

(57) ABSTRACT

Some embodiments of the invention include inventive compounds (e.g., compounds of Formula (I)). Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer). Further embodiments include methods for making the inventive compounds. Additional embodiments of the invention are also discussed herein.

55 Claims, 10 Drawing Sheets

(56) References Cited

OTHER PUBLICATIONS

Ghosh et al., "Discovery of 4-(4-(2-((5-Hydroxy-1,2,3,4-tetrahydronaphthalen-2-yl)(propyl)amino )ethyl)piperazin-1-yl) quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease" J. Med. Chem. (2010) vol. 53, pp. 2114-2125.
Goidts et al., "RNAi screening in glioma stem-like cells identifies PFKFB4 as a key molecule important for cancer cell survival" Oncogene (2012) vol. 31, No. 27, pp. 3235-3243.
Hasemann et al., "The crystal structure of the bifunctional enzyme 6-phosphofructo-2-kinase/fructose-2,6-bisphosphatase reveals distinct domain homologies" Structure (1996) vol. 4, No. 9, pp. 1017-1029.
Jain "Surflex: fully automatic flexible molecular docking using a molecular similarity-based search engine" J Med Chem (2003) vol. 46, No. 4, pp. 499-511.
Johnson et al., "Relationships between drug activity in NCI preclinical in vitro and in vivo models and early clinical trials" British Journal of Cancer (2001) vol. 84, No. 10, pp. 1424-1431.
Kemp et al., "Allosteric regulatory properties of muscle phosphofructokinase" Mol Cell Biochem (1983) vol. 57, No. 2, pp. 147-154.
Kemp et al., "Evolution of the allosteric ligand sites of mammalian phosphofructo-1-kinase" Biochemistry (2002), vol. 11, No. 30, pp. 9426-9430.
Madrid et al. (2005) "Synthesis of ring-substituted 4-aminoquinolines and evaluation of their antimalarial activities" Bioorg. Med. Chem. Lett., vol. 15, pp. 1015-1018.
Minchenko et al., "Hypoxic regulation of the 6-phosphofructo-2-kinase/fructose-2,6-bisphosphatase gene family (PFKFB-1-4) expression in vivo" FEBS letters (2003) vol. 554, No. 3, pp. 264-270.
Minchenko et al., "6-Phosphofructo-2-kinase/fructose-2,6-bisphosphatase gene family overexpression in human lung tumor" Ukr Biokhim Zh (2005) vol. 77, No. 6, pp. 46-50.
Minchenko et al., "Expression and hypoxia-responsiveness of 6-phosphofructo-2-kinase/fructose-2,6-bisphosphatase 4 in mammary gland malignant cell lines" Acta biochimica Polonica (2005) vol. 52, No. 4, pp. 881-888.
Minchenko et al., "Overexpression of 6-phosphofructo-2-kinase/fructose-2,6-bisphosphatase-4 in the human breast and colon malignant tumors" Biochimie (2005) vol. 87, No. 11, pp. 1005-1010.
Mlakar et al., "Citrate inhibition-resistant form of 6-phosphofructo-1-kinase from Aspergillus niger" Appl Environ Microbiol (2006) vol. 72, No. 7, pp. 4515-4521.
Okuno et al., Chemical Abstracts 153:580355 (Abstract of US 20100273841) (2010), 2 pages.
Perez et al., "N-Cinnamoylated Chloroquine Analogues as Dual-Stage Antimalarial Leads" J. Med. Chem. (2013) vol. 56, pp. 556-567.
PubChem Substance record SID 35997106 (2007), 5 pages.
PubChem Substance record SID 128585143 (2011), 7 pages.
PubChem Substance record SID 236909839 (2015), 7 pages.
PubChem Substance record SID 236984397 (2015), 7 pages.
PubChem Substance record SID 4060327 (2005), 1 page.
Ros et al., "Functional metabolic screen identifies 6-phosphofructo-2-kinase/fructose-2,6-biphosphatase 4 as an important regulator of prostate cancer cell survival" Cancer Discov (2012) vol. 2, No. 4, pp. 328-343.
Sakata et al., "Molecular cloning of the DNA and expression and characterization of rat testes fructose-6-phosphate,2-kinase: fructose-2,6-bisphosphatase" J Biol Chem (1991) vol. 266, No. 24, pp. 15764-15770.
Sali et al., "Comparative protein modeling by satisfaction of spatial restraints" J Mol Biol (1993) vol. 234, No. 3, pp. 779-815.
Sasaki et al., "The cell cycle associated change of the Ki-67 reactive nuclear antigen expression" J Cell Physiol (1987) vol. 133, No. 3, pp. 579-584.
Sausville, et al., "Contributions of Human Tumor Xenografts to Anticancer Drug Development" Cancer Res. (2006) vol. 66, No. 7, pp. 3351-3354.
Solomon et al. (2011) "Quinoline as a Privileged Scaffold in Cancer Drug Discovery" Current Medicinal Chemistry, vol. 18, No. 10, pp. 1488-1508.
Telang et al. (2015) "Targeting 6-Phosphofructo-2-klnase/Fructose-2,6-Blsphosphatase-4 (PFKFB4) In Cancer" FASEB abstract, vol. 29, No. 1 supplement, Abstract 725.29 (1 page).
Van Schaftingen et al., "Fructose 2,6-bisphosphate, the probably structure of the glucose- and glucagon-sensitive stimulator of phosphofructokinase" Biochem J (1980), vol. 192, No. 3, pp. 897-901.
Van Schaftingen et al., "Synthesis of a stimulator of phosphofructokinase, most likely fructose 2,6-bisphosphate, from phosphoric acid and fructose 6-phosphoric acid" Biochem Biophys Res Commun (1980) vol. 96, No. 4, 1524-1531.
Van Schaftingen et al., "A kinetic study of pyrophosphate: fructose-6-phosphate phosphotransferase from potato tubers. Application to a microassay of fructose 2,6-bisphosphate" Eur J Biochem (1982) vol. 129, No. 1, pp. 191-195.
Williams et al., Foye's Principles of Medicinal Chemistry, 5th edition, pp. 50 and 59-61, 2002.
Yalcin et al., "Nuclear targeting of 6-phosphofructo-2-kinase (PFKFB3) increases proliferation via cyclin-dependent kinases" J Biol Chem (2009) vol. 284, No. 36, 24223-24232.
Yalcin et al., "Regulation of glucose metabolism by 6-phosphofructo-2-kinase/fructose-2,6-bisphosphatases in cancer" Exp Mol Pathol (2009) vol. 86, No. 3, pp. 174-179.
Yalcin et al., "6-Phosphofructo-2-kinase (PFKFB3) promotes cell cycle progression and suppresses apoptosis via Cdkl-mediated phosphorylation of p27" Cell death & disease (2014) No. 5, Article e1337, 10 pages.
Ziakas et al., "Nitric oxide releasing derivatives of tolfenamic acid with anti-inflammatory activity and safe gastrointestinal profile" Bioorg Med. Chem. (2005) vol. 13, pp. 6485-6492.
U.S. Appl. No. 15/568,751 Restriction Requirement dated May 22, 2018, 8 pages.
U.S. Appl. No. 15/568,751 Response to Restriction Requirement dated Sep. 22, 2018, 6 pages.
U.S. Appl. No. 15/568,751 nonfinal Office action dated Dec. 19, 2018, 23 pages.
U.S. Appl. No. 15/568,751 Response to nonfinal Office action dated Apr. 10, 2019, 16 pages.
U.S. Appl. No. 15/568,751 final Office action dated May 3, 2019, 20 pages.
U.S. Appl. No. 15/568,751 Response to final Office action dated Aug. 1, 2019, 19 pages.
U.S. Appl. No. 15/568,751 nonfinal Office action dated Sep. 19, 2019, 18 pages.
U.S. Appl. No. 15/568,751 Response to nonfinal Office action dated Dec. 18, 2019, 18 pages.
U.S. Appl. No. 15/568,751 Interview Summary dated Dec. 23, 2019, 3 pages.
U.S. Appl. No. 15/568,751 Notices of Allowance and Allowability dated Apr. 2, 2020, 11 pages.
U.S. Appl. No. 16/170,391 Restriction Requirement dated May 23, 2019, 9 pages.
U.S. Appl. No. 16/170,391 Response to Restriction Requirement dated Aug. 27, 2019, 6 pages.
U.S. Appl. No. 16/170,391 Nonfinal Office action dated Sep. 13, 2019, 20 pages.
U.S. Appl. No. 16/170,391 Response to Nonfinal Office action dated Dec. 12, 2019, 22 pages.
U.S. Appl. No. 16/170,391 final Office action dated Feb. 10, 2020, 14 pages.
Ayatollahi et al. (2018) "KRAS Codon 12 and 13 Mutations in Gastric Cancer in the Northeast Iran" Iran J Pathol., vol. 13, No. 2, pp. 167-172.
Boulalas et al. (2009) "Activation of RAS family genes in urothelial carcinoma" J Urol, vol. 181, No. 5, pp. 2312-2319. (Abstract only).

(56) References Cited

OTHER PUBLICATIONS

Chanput et al. (2015) in COST Action FA1005 "The Impact of Food Bio-Actives on Gut Health: In Vitro and Ex Vivo Models" Chapter 14 THP-1 and U937 Cells, Springer, New York, New York, pp. 147-159.

Chesney et al. (2013) "Regulation of Glycolytic and Mitochondrial Metabolism by Ras" Current Pharmaceutical Biotechnology, vol. 14, No. 3, pp. 251-260.

Chesney et al. (2014) "Fructose-2,6-Bisphosphate synthesis by 6-Phosphofructo-2-Kinase/Fructose-2,6-Bisphosphatase 4 (PFKFB4) is required for the glycolytic response to hypoxia and tumor growth" Oncotarget, vol. 5, No. 16, pp. 6670-6686.

Chesney et al. (2015) "Targeting the sugar metabolism of tumors with a first-in-class 6-phosphofructo-2-kinase (PFKFB4) inhibitor" Oncotarget, vol. 6, No. 20, pp. 18001-18011.

Dahmane et al. (2001) "The Sonic Hedgehog-Gli pathway regulates dorsal brain growth and tumorigenesis" Development, vol. 128, pp. 5201-5212.

Di Micco et al. (2019) "Rare sites of breast cancer metastasis: a review" Transl Cancer Res, vol. 8 (Suppl 5), pp. S518-S552.

Gandaglia et al. (2014) "Distribution of Metastatic Sites in Patients With Prostate Cancer: A Population-Based Analysis" The Prostate, vol. 74, pp. 210-216.

Kaur et al. (2016) "Tobacco Smoke and Ras Mutations Among Latino and Non-Latino-Children with Acute Lymphoblastic Leukemia" Arch Med Res, vol. 47, No. 8, pp. 677-683.

Lupi (2007) "Correlations between the Sonic Hedgehog Pathway and basal cell carcinoma" International Journal of Dermatology, vol. 46, pp. 1113-1117.

Park et al. (1996) "Biology of Colorectal and Gastric Cancer Cell Lines" Journal of Cellular Biochemistry Supplement, vol. 24, pp. 131-141.

Polom et al. (2019) "KRAS Mutation in Gastric Cancer and Prognostication Associated with Microsatellite Instability Status" Pathol. Oncol. Res., vol. 25, pp. 333-340.

Roato (2014) "Bone metastases: When and how lung cancer interacts with bone" World J Clin Oncol, vol. 5, No. 2, pp. 149-155.

Saeed et al. (2019) "RAS genes in colorectal carcinoma: pathogenesis, testing guidelines and treatment implications" J Clin Pathol, vol. 72, pp. 135-139.

Shahi et al. (2008) "Hedgehog signalling in medulloblastoma, glioblastoma and neuroblastoma" Oncology Reports, vol. 19, pp. 681-688.

Shao et al. (2022) "Breast Cancer Bone Metastasis: A Narrative Review of Emerging Targeted Drug Delivery Systems" Cells, vol. 11, Article 388 (19 pages).

Tamura et al. (2015) "Specific organ metastases and survival in metastatic non-small-cell lung cancer" Molecular and Clinical Oncology, vol. 3, pp. 217-221.

Telang et al. (2007) "The oncoprotein H-RasV12 increases mitochondrial metabolism" Molecular Cancer, vol. 6, Article 77 (14 pages).

Wang et al. (2020) "PFKFB4 is critical for the survival of acute monocytic leukemia cells" Biochemical and Biophysical Research Communications, vol. 526, pp. 978-985.

Yun et al. (2009) "Glucose Deprivation Contributes to the Development of KRAS Pathway Mutations in Tumor Cells" SCIENCE, vol. 325, pp. 1555-1559.

Boulalas et al. (2009) "Activation of RAS family genes in urothelial carcinoma" J Urol, vol. 181, No. 5, pp. 2312-2319.

U.S. Appl. No. 16/170,391 Response to Final Office action dated Apr. 13, 2020, 18 pages.

U.S. Appl. No. 16/170,391 Notices of Allowance and Allowability dated Apr. 24, 2020, 12 pages.

* cited by examiner

A

B

A

B

A

COMPOUNDS, COMPOSITIONS, METHODS FOR TREATING DISEASES, AND METHODS FOR PREPARING COMPOUNDS

CROSS-REFERENCE TO RELATED APPLICATIONS

This application is a National Stage Entry of International Application No. PCT/US2018/048660 filed Aug. 30, 2018, entitled "COMPOUNDS, COMPOSITIONS, METHODS FOR TREATING DISEASES, AND METHODS FOR PREPARING COMPOUNDS" which is herein incorporated by reference in its entirety, and which claims the benefit of U.S. Provisional Application No. 62/552,716, filed Aug. 31, 2017, entitled "Inhibitors for the Treatment of Cancer" which is herein incorporated by reference in its entirety.

U.S. Provisional Application No. 62/152,239, filed Apr. 24, 2015, entitled "Selective PFKFB4 Inhibitors for the Treatment of Cancer" is herein incorporated by reference in its entirety.

PCT Application No. PCT/US2016/028868, filed Apr. 22, 2016, entitled "Selective PFKFB4 Inhibitors for the Treatment of Cancer" and published as WO 2016/172499 A1 (Oct. 27, 2016) is herein incorporated by reference in its entirety.

GOVERNMENT RIGHTS

This invention was made with government support under pilot grant U01HL127518 awarded by the National Institutes of Health REACH Program. The government has certain rights in the invention.

BACKGROUND 6-phosphofructo-2-kinase/fructose-2,6,biphosphate 4 (PFKFB4) is a bifunctional enzyme that can increase intracellular F2,6BP and, thus, flux through PFK-1 or decrease F2,6BP and PFK-1 activity resulting in increased shunting of glucose 6-phosphate for NADPH and ribose production. PFKFB4 can be involved in neoplastic metabolism.

Several compounds are known to treat cancer, but do so inadequately.

Certain embodiments of the invention address one or more of the deficiencies described above. For example, in some embodiments of the invention, inventive compounds such as Formula (I) are disclosed. In some embodiments, PFKFB4 inhibitors are disclosed. Other embodiments include compositions (e.g., pharmaceutical compositions) comprising the inventive compound. Still other embodiments of the invention include compositions (e.g., pharmaceutical compositions) for treating, for example, certain diseases using the inventive compounds. Some embodiments include methods of using the inventive compound (e.g., in compositions or in pharmaceutical compositions) for administering and treating (e.g., diseases such as cancer). Further embodiments include methods for making the inventive compounds. Additional embodiments of the invention are also discussed herein.

SUMMARY

Some embodiments of the present invention include a compound selected from Formula (I)

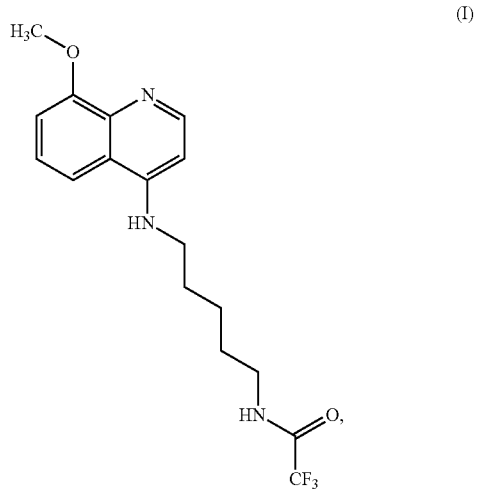 [SMILES: COc1cccc2c(NCCCCCNC(=O)C(F)(F)F)ccnc12]

salts, optical isomers, geometric isomers, salts of isomers, and derivatives thereof. In other embodiments, the compound is a salt of Formula (I). In yet other embodiments, the compound is Formula (I).

Some embodiments of the present invention include a composition comprising any compound disclosed herein (e.g., Formula (I)). In other embodiments, the composition comprises an amount of the compound that is from about 0.0001% (by weight total composition) to about 99%. In still other embodiments, the composition further comprises a formulary ingredient, an adjuvant, or a carrier.

Some embodiments of the present invention include a pharmaceutical composition comprising any compound disclosed herein (e.g., Formula (I)). In other embodiments, the pharmaceutical composition comprises an amount of the compound from about 0.0001% (by weight total composition) to about 50%. In still other embodiments, the pharmaceutical composition further comprises a formulary ingredient, an adjuvant, or a carrier.

Some embodiments of the present invention include a method for providing an animal with a compound comprising one or more administrations of one or more compositions comprising any compound disclosed herein (e.g., Formula (I)), wherein the compositions may be the same or different if there is more than one administration. In other embodiments, the method can have at least one of the one or more compositions further comprising a formulary ingredient. In still other embodiments, at least one of the one or more compositions comprises any composition disclosed herein or any pharmaceutical composition disclosed herein. In yet other embodiments, at least one of the one or more administrations comprises parenteral administration, mucosal administration, intravenous administration, subcutaneous administration, topical administration, intradermal administration, oral administration, sublingual administration, intranasal administration, or intramuscular administration. In some embodiments, if there is more than one administration at least one composition used for at least one administration is different from the composition of at least one other administration. In other embodiments, the compound of at least one of the one or more compositions is administered to the animal in an amount of from about 0.01 mg/kg animal body weight to about 150 mg/kg animal body weight. In still other embodiments, the animal is a human, a rodent, or a primate.

Some embodiments of the present inventions include a method for treating an animal for a disease, comprising one or more administrations of one or more compositions comprising any compound disclosed herein (e.g., Formula (I)), wherein the compositions may be the same or different if there is more than one administration. In other embodiments, at least one of the one or more compositions further comprises a formulary ingredient. In yet other embodiments, at least one of the one or more compositions comprises any composition disclosed herein or any pharmaceutical composition disclosed herein. In still other embodiments, at least one of the one or more administrations comprises parenteral administration, mucosal administration, intravenous administration, subcutaneous administration, topical administration, intradermal administration, oral administration, sublingual administration, intranasal administration, or intramuscular administration. In certain embodiments, if there is more than one administration at least one composition used for at least one administration is different from the composition of at least one other administration. In some embodiments, the compound of at least one of the one or more compositions is administered to the animal in an amount of from about 0.005 mg/kg animal body weight to about 150 mg/kg animal body weight. In other embodiments, the animal is a human, a rodent, or a primate. In still other embodiments, the animal is in need of the treatment. In yet other embodiments, the method is for treating cancer. In certain embodiments, the method is for treating acute lymphoblastic leukemia, astrocytoma, basal cell carcinoma, bladder cancer, bone marrow cancer, brain cancer, brain tumors, childhood brain tumors, breast cancer, chronic lymphocytic leukemia (CLL), CNS cancer, glioblastoma, glioblastoma multiforme, gliosarcoma, astrocytoma, colon cancer, colorectal cancer, colon cancer, rectal cancer, endometrial cancer, gastric cancer, glioblastoma, glioblastoma multiforme, glioma, gliosarcoma, hepatocellular carcinoma, kidney cancer, renal cancer, leukemia, liver cancer, lung cancer, non-small cell lung cancer, lymphoma, melanoma, cutaneous malignant melanoma, melanoma tumorigenesis, malignancies, hematological malignancies, malignant nerve sheath tumors, medulloblastoma, meningioma, multiple myeloma, nasopharyngeal carcinoma, neuroblastoma, non-Hodgkin lymphoma, diffuse large B-cell lymphoma, non-small cell lung cancer, oral cancer, ovarian cancer, pancreatic cancer, pancreatic ductal adenocarcinoma, prostate cancer, rectal cancer, renal cancer, renal cell carcinoma, rhabdomyosarcoma, squamous cell carcinoma, head and neck squamous cell carcinoma, stomach cancer, thyroid cancer, uterine cancer, cancers that can result in metastasis, cancers resulting from metastasis, or cancerous tumors thereof. In some embodiments, the method is for treating breast cancer, childhood brain tumors, hematological malignancies, leukemia, melanoma, lung cancer, colon cancer, prostate cancer, or cancerous tumors thereof. In other embodiments, the method is for treating breast cancer, childhood brain tumors, hematological malignancies, leukemia, melanoma, lung cancer, colon cancer, or prostate cancer.

Some embodiments of the present invention include a method of inhibiting PFKFB4 in a cell, the method comprising contacting the cell with any compound disclosed herein (e.g., Formula (I)). In other embodiments, PFKFB4 is specifically inhibited. In still other embodiments, the cell is a mammalian cell. In yet other embodiments, the cell is a cancer cell. In some embodiments, the cell is H460, H1299, H441, H522, DAOY, D283, SKBR3, Jurkat, B16F10, A549, MDA-MB-231, LNCaP, HCT116, or LLC cell line.

Some embodiments of the present invention include a method of inhibiting PFKFB4 in a subject, the method comprising administering to the subject an effective amount of any compound disclosed herein (e.g., Formula (I)). In other embodiments, the compound is administered at a dosage effective for specifically inhibiting PFKFB4. In still other embodiments, the compound is administered orally or administered intravenously. In yet other embodiments, the subject has cancer. In some embodiments, the subject has breast cancer, childhood brain tumors, hematological malignancies, leukemia, melanoma, lung cancer, colon cancer, prostate cancer, or cancerous tumors thereof. In other embodiments, the method treats cancer in the subject. In still other embodiments, the method treats breast cancer, childhood brain tumors, hematological malignancies, leukemia, melanoma, lung cancer, colon cancer, prostate cancer, or cancerous tumors thereof, in the subject. In yet other embodiments, the subject remains substantially free of signs of toxicity.

Some embodiments of the present invention include a method of reducing glycolytic flux in a cell, the method comprising contacting the cell with an effective amount of any compound disclosed herein (e.g., Formula (I)). In other embodiments, the cell is a mammalian cell. In still other embodiments, the cell is a cancer cell. In yet other embodiments, the cell is H460, H1299, H441, H522, DAOY, D283, SKBR3, Jurkat, B16F10, A549, MDA-MB-231, LNCaP, HCT116, or LLC cell line.

Some embodiments of the present invention include a method of reducing proliferative capacity of a cell, the method comprising contacting the cell with an effective amount of any compound disclosed herein (e.g., Formula (I)). In some embodiments, the cell is contacted with the compound at a dosage effective for specifically inhibiting PFKFB4. In other embodiments, the cell is a mammalian cell. In still other embodiments, the cell is a cancer cell. In still other embodiments, the cell is H460, H1299, H441, H522, DAOY, D283, SKBR3, Jurkat, B16F10, A549, MDA-MB-231, LNCaP, HCT116, or LLC cell line.

Some embodiments of the present invention include a method of reducing fructose-2,6-bisphosphate (F2,6BP) in a cell, the method comprising contacting the cell with an effective amount of any compound disclosed herein (e.g., Formula (I)). In other embodiments, the cell is a mammalian cell. In still other embodiments, the cell is a cancer cell.

Some embodiments of the present invention include a method for preparing any compound disclosed herein (e.g., Formula (I)), comprising, (a) reacting a compound of Formula (II) with a compound of Formula (III) to result in a mixture comprising a compound of Formula (IV); (b) reacting a compound of Formula (IV) with a compound of Formula (V); and; (c) recovering any compound disclosed herein (e.g., Formula (I)), wherein Formula (II) is

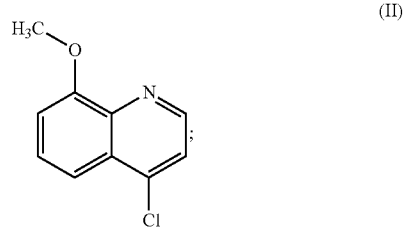

(II)

Formula (III) is

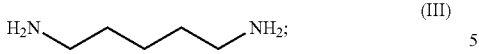

Formula (IV) is

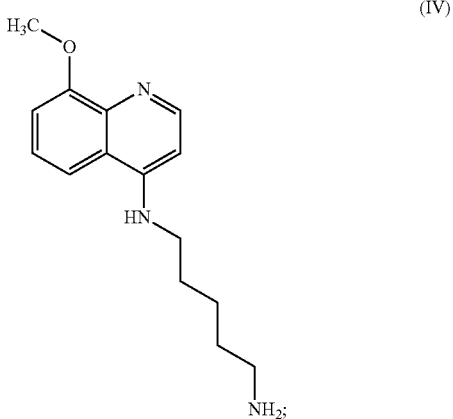 [SMILES: COc1cccc2c(NCCCCCN)ccnc12]

and
Formula (V) is

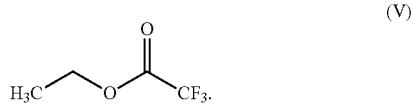

In certain embodiments, the method is for preparing Formula (I).

Other embodiments of the invention are also discussed herein.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

DETAILED DESCRIPTION

Figure 1:
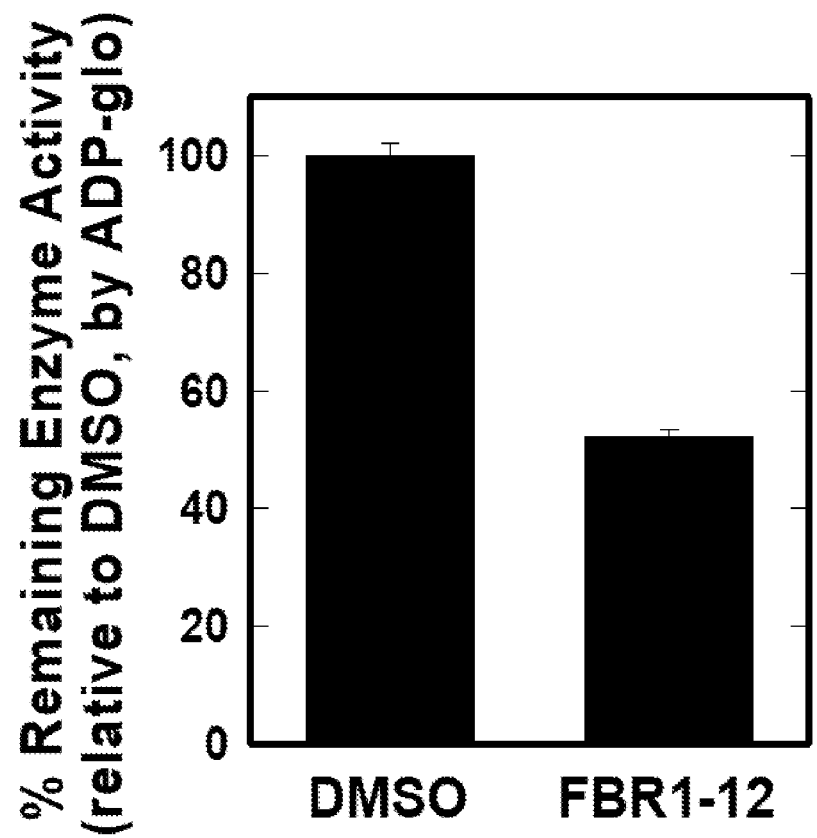
FIG. 1: Inhibiting 6-phosphofructo-2-kinase/fructose-2,6, biphosphate 4 (PFKFB4) activity by Formula (I) (also referred to as FBR1-12).

While embodiments encompassing the general inventive concepts may take diverse forms, various embodiments will be described herein, with the understanding that the present disclosure is to be considered merely exemplary, and the general inventive concepts are not intended to be limited to the disclosed embodiments.

Some embodiments of the invention include inventive compounds (e.g., compounds of Formula (I)). Other embodiments include compositions (e.g., pharmaceutical compositions) comprising the inventive compound. Still other embodiments of the invention include compositions for treating, for example, certain diseases using the inventive compounds. Some embodiments include methods of using the inventive compound (e.g., in compositions or in pharmaceutical compositions) for administering and treating. Further embodiments include methods for making the inventive compound. Additional embodiments of the invention are also discussed herein.

As used herein (unless otherwise specified), the term "halogen" means monovalent Cl, F, Br, or I.

As used herein (unless otherwise specified), the term "hetero atom" means an atom selected from nitrogen atom, oxygen atom, or sulfur atom.

As used herein (unless otherwise specified), the terms "hydroxy" or "hydroxyl" indicates the presence of a monovalent —OH group.

Compounds and Compositions Including Pharmaceutical Compositions

Some embodiments of the invention include compounds of Formula (I):

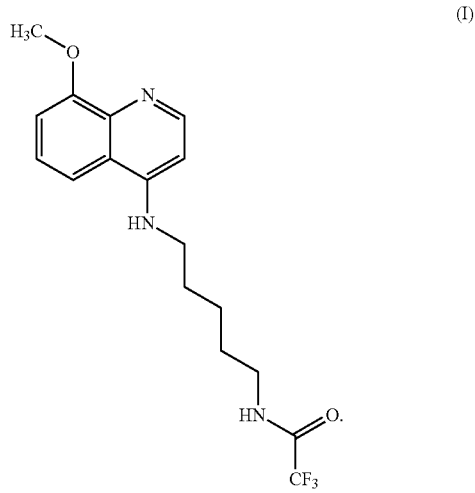 [SMILES: COc1cccc2c(NCCCCCNC(=O)C(F)(F)F)ccnc12]

Formula (I) is also referred to herein as "FBR1-12" and has the chemical name 2,2,2-trifluoro-N-(5-((8-methoxyquinolin-4-yl)amino)pentyl)acetamide.

In some embodiments, the compounds of Formula (I) can be in the form of salts, optical and geometric isomers, and salts of isomers. In other embodiments, the compounds can be in various forms, such as uncharged molecules, components of molecular complexes, or non-irritating pharmacologically acceptable salts, including but not limited to hydrochloride, hydrobromide, sulphate, phosphate, nitrate, borate, acetate, maleate, tartrate, and salicylate. In some instances, for acidic compounds, salts can include metals, amines, or organic cations (e.g. quaternary ammonium). In yet other embodiments, simple derivatives of the compounds (e.g., ethers, esters, or amides) which have desirable retention and release characteristics, but which are easily hydrolyzed by body pH, enzymes, or other suitable means, can be employed.

In some embodiments, the compounds of the invention (e.g., Formula (I)) can inhibit the activity of PFKFB4. In some embodiments, the compounds of the invention (e.g., Formula (I)) can specifically inhibit the activity of PFKFB4. In some embodiments, "specifically inhibiting" (and other variations of inhibiting, such as "specifically inhibited") is defined as inhibiting PFKFB4 without inhibiting 6-phosphofructo-2-kinase/fructose-2,6,biphosphate 3 (PFKFB3), 6-phosphofructo-2-kinase/fructose-2,6-biphospatase 2 (PFKFB2), or 6-phosphofructo-2-kinase/fructose-2,6,biphosphate 1 (PFKFB1). Thus, in certain embodiments, a compound of the invention is a specific inhibitor of the activity of PFKFB4. In some aspects, a compound of the invention inhibits the activity of PFKFB4 by at least about 25%, about 30%, about 35%, about 40%, about 45%, about 50%, about 55%, about 60%, about 65%, about 70%, about 75%, about 80%, about 85%, about 90%, about 95% about 99%, or any value or range in between, but does not inhibit the activity of PFKFB1, PFKFB2, or PFKFB3 by more than about 20%, about 15%, about 10%, about 5%, about 2%, or about 1%. In certain embodiments, the compounds of the invention (e.g., Formula (I)) can decrease fructose-2,6 bisphosphate production in a cell (e.g., a cancer cell). In some embodiments, the compounds of the invention (e.g., Formula (I)) can decrease fructose-2,6 bisphosphate in a cell (e.g., a cancer cell). In other embodiments, the compounds of the invention (e.g., Formula (I)) can decrease proliferation of a cell (e.g., a cancer cell). In some embodiments, the compounds of the invention (e.g., Formula (I)) can decrease glycolysis in a cell (e.g., a cancer cell).

In other embodiments, the compounds of the invention (e.g., Formula (I)) can decrease glycolytic flux in a cell (e.g., a cancer cell). In still other embodiments, the compounds of the invention (e.g., Formula (I)) can decrease ATP production in a cell (e.g., a cancer cell). In other embodiments, the compounds of the invention (e.g., Formula (I)) can decrease ATP in a cell (e.g., a cancer cell). In yet other embodiments, the compounds of the invention (e.g., Formula (I)) can decrease anchorage independent growth of a cell (e.g., a cancer cell).

In certain embodiments, one or more compounds of the invention (e.g., Formula (I)) can be part of a composition and can be in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, or no more than about 99.99%, from about 0.0001% to about 99%, from about 0.0001% to about 50%, from about 0.01% to about 95%, from about 1% to about 95%, from about 10% to about 90%, or from about 25% to about 75%.

In some embodiments, one or more compounds of the invention (e.g., Formula (I)) can be purified or isolated in an amount (by weight of the total composition) of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.0001% to about 99%, from about 0.0001% to about 50%, from about 0.01% to about 95%, from about 1% to about 95%, from about 10% to about 90%, or from about 25% to about 75%.

Some embodiments of the present invention include compositions comprising one or more compounds of the invention (e.g., Formula (I)). In certain embodiments, the composition is a pharmaceutical composition, such as compositions that are suitable for administration to animals (e.g., mammals, primates, monkeys, humans, canine, feline, porcine, mice, rabbits, or rats). In some instances, the pharmaceutical composition is non-toxic, does not cause side effects, or both. In some embodiments, there may be inherent side effects (e.g., it may harm the patient or may be toxic or harmful to some degree in some patients).

"Therapeutically effective amount" means an amount effective to achieve a desired and/or beneficial effect. An effective amount can be administered in one or more administrations. For some purposes of this invention, a therapeutically effective amount is an amount appropriate to treat an indication. By treating an indication is meant achieving any desirable effect, such as one or more of palliate, ameliorate, stabilize, reverse, slow, or delay disease progression, increase the quality of life, or to prolong life. Such achievement can be measured by any suitable method, such as measurement of tumor size.

In some embodiments, one or more compounds of the invention (e.g., Formula (I)) can be part of a pharmaceutical composition and can be in an amount of at least about 0.0001%, at least about 0.001%, at least about 0.10%, at least about 0.15%, at least about 0.20%, at least about 0.25%, at least about 0.50%, at least about 0.75%, at least about 1%, at least about 10%, at least about 25%, at least about 50%, at least about 75%, at least about 90%, at least about 95%, at least about 99%, at least about 99.99%, no more than about 75%, no more than about 90%, no more than about 95%, no more than about 99%, no more than about 99.99%, from about 0.001% to about 99%, from about 0.001% to about 50%, from about 0.1% to about 99%, from about 1% to about 95%, from about 10% to about 90%, or from about 25% to about 75%. In some embodiments, the pharmaceutical composition can be presented in a dosage form which is suitable for the topical, subcutaneous, intrathecal, intraperitoneal, oral, parenteral, rectal, cutaneous, nasal, vaginal, or ocular administration route. In other embodiments, the pharmaceutical composition can be presented in a dosage form which is suitable for parenteral administration, mucosal administration, intravenous administration, subcutaneous administration, topical administration, intradermal administration, oral administration, sublingual administration, intranasal administration, or intramuscular administration. The pharmaceutical composition can be in the form of, for example, tablets, capsules, pills, powders granulates, suspensions, emulsions, solutions, gels (including hydrogels), pastes, ointments, creams, plasters, drenches, delivery devices, suppositories, enemas, injectables, implants, sprays, aerosols or other suitable forms.

In some embodiments, the pharmaceutical composition can include one or more formulary ingredients. A "formulary ingredient" can be any suitable ingredient (e.g., suitable for the drug(s), for the dosage of the drug(s), for the timing of release of the drugs(s), for the disease, for the disease state, or for the delivery route) including, but not limited to, water (e.g., boiled water, distilled water, filtered water, pyrogen-free water, or water with chloroform), sugar (e.g., sucrose, glucose, mannitol, sorbitol, xylitol, or syrups made therefrom), ethanol, glycerol, glycols (e.g., propylene glycol), acetone, ethers, DMSO, surfactants (e.g., anionic surfactants, cationic surfactants, zwitterionic surfactants, or nonionic surfactants (e.g., polysorbates)), oils (e.g., animal oils, plant oils (e.g., coconut oil or *arachis* oil), or mineral oils), oil derivatives (e.g., ethyl oleate, glyceryl monostearate, or hydrogenated glycerides), excipients, preservatives (e.g., cysteine, methionine, antioxidants (e.g., vitamins (e.g., A, E, or C), selenium, retinyl palmitate, sodium citrate, citric acid, chloroform, or parabens, (e.g., methyl paraben or propyl paraben)), or combinations thereof.

In certain embodiments, pharmaceutical compositions can be formulated to release the active ingredient (e.g., one or more compounds of the invention such as Formula (I)) substantially immediately upon the administration or any substantially predetermined time or time after administration. Such formulations can include, for example, controlled release formulations such as various controlled release compositions and coatings.

Other formulations (e.g., formulations of a pharmaceutical composition) can, in certain embodiments, include those incorporating the drug (or control release formulation) into food, food stuffs, feed, or drink.

Other embodiments of the invention can include methods of administering or treating an organism, which can involve treatment with an amount of at least one compound of the invention (e.g., Formula (I)) that is effective to treat the disease, condition, or disorder that the organism has, or is suspected of having, or is susceptible to, or to bring about a desired physiological effect. In some embodiments, the composition or pharmaceutical composition comprises at least one compound of the invention (e.g., Formula (I)) which can be administered to an animal (e.g., mammals, primates, monkeys, or humans) in an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In some embodiments, the dosage can be from about 0.01 mg/kg body weight to about 150 mg/kg body weight. In some embodiments, the dosage can be from about 0.005 mg/kg body weight to about 150 mg/kg body weight. In some embodiments, the dosage can be about 0.5 mg/kg human body weight or about 6.5 mg/kg human body weight. In some instances, some animals (e.g., mammals, mice, rabbits, feline, porcine, or canine) can be administered a dosage of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, the dosage can be from about 0.01 mg/kg body weight to about 150 mg/kg body weight. In some embodiments, the dosage can be from about 0.005 mg/kg body weight to about 150 mg/kg body weight. Of course, those skilled in the art will appreciate that it is possible to employ many concentrations in the methods of the present invention, and using, in part, the guidance provided herein, will be able to adjust and test any number of concentrations in order to find one that achieves the desired result in a given circumstance. In other embodiments, the compounds of the invention (e.g., Formula (I)) can be administered in combination with one or more other therapeutic agents for a given disease, condition, or disorder.

In some embodiments, the compositions can include a unit dose of one or more compounds of the invention (e.g., Formula (I)) in combination with a pharmaceutically acceptable carrier and, in addition, can include other medicinal agents, pharmaceutical agents, carriers, adjuvants, diluents, and excipients. In certain embodiments, the carrier, vehicle or excipient can facilitate administration, delivery and/or improve preservation of the composition. In other embodiments, the one or more carriers, include but are not limited to, saline solutions such as normal saline, Ringer's solution, PBS (phosphate-buffered saline), and generally mixtures of various salts including potassium and phosphate salts with or without sugar additives such as glucose. Carriers can include aqueous and non-aqueous sterile injection solutions that can contain antioxidants, buffers, bacteriostats, bactericidal antibiotics, and solutes that render the formulation isotonic with the bodily fluids of the intended recipient; and aqueous and non-aqueous sterile suspensions, which can include suspending agents and thickening agents. In other embodiments, the one or more excipients can include, but are not limited to water, saline, dextrose, glycerol, ethanol, or the like, and combinations thereof. Nontoxic auxiliary substances, such as wetting agents, buffers, or emulsifiers may also be added to the composition. Oral formulations can include such normally employed excipients as, for example, pharmaceutical grades of mannitol, lactose, starch, magnesium stearate, sodium saccharine, cellulose, and magnesium carbonate.

Administration Routes and Treatments of Disease

The compounds of the invention (e.g., Formula (I)) can be administered to animals by any number of suitable administration routes or formulations. The compounds of the invention (e.g., Formula (I)) can also be used to treat animals for a variety of diseases. Animals include but are not limited to mammals, primates, monkeys (e.g., macaque, rhesus macaque, or pig tail macaque), humans, canine, feline, bovine, porcine, avian (e.g., chicken), mice, rabbits, and rats. As used herein, the term "subject" refers to both human and animal subjects.

The route of administration of the compounds of the invention (e.g., Formula (I)) can be of any suitable route. Administration routes can be, but are not limited to the oral route, the parenteral route, the cutaneous route, the nasal route, the rectal route, the vaginal route, and the ocular route. In other embodiments, administration routes can be parenteral administration, mucosal administration, intravenous administration, subcutaneous administration, topical administration, intradermal administration, oral administration, sublingual administration, intranasal administration, or intramuscular administration. The choice of administration route can depend on the compound identity (e.g., the physical and chemical properties of the compound) as well as the age and weight of the animal, the particular disease (e.g., cancer), and the severity of the disease (e.g., stage or severity of cancer). Of course, combinations of administration routes can be administered, as desired.

Some embodiments of the invention include a method for providing a subject with a composition comprising one or more compounds of the invention (e.g., Formula (I)) described herein (e.g., a pharmaceutical composition) which comprises one or more administrations of one or more such compositions; the compositions may be the same or different if there is more than one administration.

Diseases that can be treated in an animal (e.g., mammals, porcine, canine, avian (e.g., chicken), bovine, feline, primates, rodents, monkeys, rabbits, mice, rats, and humans) using a compound of the invention (e.g., Formula (I)) include, but are not limited to cancers.

In some embodiments, cancers that can be treated in an animal (e.g., mammals, porcine, canine, avian (e.g., chicken), bovine, feline, primates, rodents, monkeys, rabbits, mice, rats, and humans) using (e.g., by administering) a compound of the invention (e.g., Formula (I)) include, but are not limited to, acute lymphoblastic leukemia, astrocytoma, basal cell carcinoma, bladder cancer, bone marrow cancer, brain cancer, brain tumors (e.g., childhood brain tumors), breast cancer, chronic lymphocytic leukemia (CLL), CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, hepatocellular carcinoma, kidney cancer (e.g., renal cancer), leukemia, liver cancer, lung cancer (e.g., non-small cell lung cancer), lymphoma, melanoma (e.g., cutaneous malignant melanoma or melanoma tumorigenesis), malignancies (e.g., hematological malignancies), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In some embodiments, cancers that can be treated include, but are not limited to breast cancer, childhood brain tumors, hematological malignancies, leukemia, melanoma, lung cancer, colon cancer, prostate cancer, or cancerous tumors thereof. In some embodiments, cancers that can be treated include, but are not limited to breast cancer, childhood brain tumors, hematological malignancies, leukemia, melanoma, lung cancer, colon cancer, or prostate cancer. Animals that can be treated include but are not limited to mammals, rodents, primates, monkeys (e.g., macaque, rhesus macaque, pig tail macaque), humans, canine, feline, porcine, avian (e.g., chicken), bovine, mice, rabbits, and rats. As used herein, the term "subject" refers to both human and animal subjects. In some instances, the animal is in need of the treatment (e.g., by showing signs of disease or cancer, or by having a cancerous tumor).

In some embodiments, cancers that can be treated in an animal (e.g., mammals, porcine, canine, avian (e.g., chicken), bovine, feline, primates, rodents, monkeys, rabbits, mice, rats, and humans) using a compound of the invention (e.g., Formula (I)) include, but are not limited to cancers that can be treated by inhibiting (e.g., reducing the activity or expression of) 6-phosphofructo-2-kinase/fructose-2,6-biphosphatase 4 (PFKFB4). In some embodiments, cancers that can be treated in an animal include cancers that can be treated by specifically inhibiting PFKFB4. In some embodiments, "specifically inhibiting" (and other variations of inhibiting, such as "specifically inhibited") is defined as inhibiting PFKFB4 without inhibiting 6-phosphofructo-2-kinase/fructose-2,6,biphosphate 3 (PFKFB3), 6-phosphofructo-2-kinase/fructose-2,6-biphospatase 2 (PFKFB2), or 6-phosphofructo-2-kinase/fructose-2,6,biphosphate 1 (PFKFB1). Thus, in certain embodiments, a compound of the invention is a specific inhibitor of the activity of PFKFB4. In some aspects, a compound of the invention inhibits the activity of PFKFB4 by at least about 25%, about 30%, about 35%, about 40%, about 45%, about 50%, about 55%, about 60%, about 65%, about 70%, about 75%, about 80%, about 85%, about 90%, about 95% about 99%, or any value or range in between, but does not inhibit the activity of PFKFB1, PFKFB2, or PFKFB3 by more than about 20%, about 15%, about 10%, about 5%, about 2%, or about 1%.

As used herein, the term "treating" (and its variations, such as "treatment") is to be considered in its broadest context. In particular, the term "treating" does not necessarily imply that an animal is treated until total recovery. Accordingly, "treating" includes amelioration of the symptoms, relief from the symptoms or effects associated with a condition, decrease in severity of a condition, or preventing, preventively ameliorating symptoms, or otherwise reducing the risk of developing a particular condition. As used herein, reference to "treating" an animal includes but is not limited to prophylactic treatment and therapeutic treatment. Any of the compositions (e.g., pharmaceutical compositions) described herein can be used to treat an animal.

As related to treating cancer (e.g., breast cancer, childhood brain tumors, hematological malignancies, leukemia, melanoma, lung cancer, colon cancer, prostate cancer, or cancerous tumors thereof), treating can include but is not limited to prophylactic treatment and therapeutic treatment. As such, treatment can include, but is not limited to: preventing cancer (e.g., breast cancer, childhood brain tumors, hematological malignancies, leukemia, melanoma, lung cancer, colon cancer, prostate cancer, or cancerous tumors thereof); reducing the risk of cancer (e.g., breast cancer, childhood brain tumors, hematological malignancies, leukemia, melanoma, lung cancer, colon cancer, prostate cancer, or cancerous tumors thereof); ameliorating or relieving symptoms of cancer (e.g., breast cancer, childhood brain tumors, hematological malignancies, leukemia, melanoma, lung cancer, colon cancer, prostate cancer, or cancerous tumors thereof); eliciting a bodily response against cancer (e.g., breast cancer, childhood brain tumors, hematological malignancies, leukemia, melanoma, lung cancer, colon cancer, prostate cancer, or cancerous tumors thereof); inhibiting the development or progression of cancer (e.g., breast cancer, childhood brain tumors, hematological malignancies, leukemia, melanoma, lung cancer, colon cancer, prostate cancer, or cancerous tumors thereof); inhibiting or preventing the onset of symptoms associated with cancer (e.g., breast cancer, childhood brain tumors, hematological malignancies, leukemia, melanoma, lung cancer, colon cancer, prostate cancer, or cancerous tumors thereof); reducing the severity of cancer (e.g., breast cancer, childhood brain tumors, hematological malignancies, leukemia, melanoma, lung cancer, colon cancer, prostate cancer, or cancerous tumors thereof); causing a regression of cancer (e.g., breast cancer, childhood brain tumors, hematological malignancies, leukemia, melanoma, lung cancer, colon cancer, prostate cancer, or cancerous tumors thereof) or one or more of the symptoms associated with cancer (e.g., a decrease in tumor size); causing remission of cancer (e.g., breast cancer, childhood brain tumors, hematological malignancies, leukemia, melanoma, lung cancer, colon cancer, prostate cancer, or cancerous tumors thereof); or preventing relapse of cancer (e.g., breast cancer, childhood brain tumors, hematological malignancies, leukemia, melanoma, lung cancer, colon cancer, prostate cancer, or cancerous tumors thereof). In some embodiments, treating does not include prophylactic treatment of cancer (e.g., preventing or ameliorating future cancer).

Treatment of an animal can occur using any suitable administration method (such as those disclosed herein) and using any suitable amount of a compound of the invention (e.g., Formula (I)). In some embodiments, methods of treatment comprise treating an animal for cancer (e.g., breast cancer, childhood brain tumors, hematological malignancies, leukemia, melanoma, lung cancer, colon cancer, prostate cancer, or cancerous tumors thereof). Some embodiments of the invention include a method for treating a subject (e.g., an animal such as a human or primate) with a composition comprising a compound of the invention (e.g., Formula (I)) (e.g., a pharmaceutical composition) which comprises one or more administrations of one or more such compositions; the compositions may be the same or different if there is more than one administration.

In some embodiments, the method of treatment includes administering an effective amount of a composition comprising a compound of the invention (e.g., Formula (I)). As used herein, the term "effective amount" refers to a dosage or a series of dosages sufficient to affect treatment (e.g., to treat cancer, such as but not limited to breast cancer, childhood brain tumors, hematological malignancies, leukemia, melanoma, lung cancer, colon cancer, prostate cancer, or cancerous tumors thereof) in an animal. In some embodiments, an effective amount can encompass a therapeutically effective amount, as disclosed herein. In certain embodiments, an effective amount can vary depending on the subject and the particular treatment being affected. The exact amount that is required can, for example, vary from subject to subject, depending on the age and general condition of the subject, the particular adjuvant being used (if applicable), administration protocol, and the like. As such, the effective amount can, for example, vary based on the particular circumstances, and an appropriate effective amount can be determined in a particular case. An effective amount can, for example, include any dosage or composition amount disclosed herein. In some embodiments, an effective amount of at least one compound of the invention (e.g., Formula (I)) (which can be administered to an animal such as mammals, primates, monkeys or humans) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 0.5 mg/kg, about 1 mg/kg, about 3 mg/kg, about 5 mg/kg, about 5.5 mg/kg, about 6 mg/kg, about 6.5 mg/kg, about 7 mg/kg, about 7.5 mg/kg, about 8 mg/kg, about 10 mg/kg, about 12 mg/kg, or about 15 mg/kg. In some embodiments, the dosage can be from about 0.01 mg/kg body weight to about 150 mg/kg body weight. In some embodiments, the dosage can be from about 0.005 mg/kg body weight to about 150 mg/kg body weight. In regard to some embodiments, the dosage can be about 0.5 mg/kg human body weight or about 6.5 mg/kg human body weight. In some instances, an effective amount of at least one compound of the invention (e.g., Formula (I)) (which can be administered to an animal such as mammals, rodents, mice, rabbits, feline, porcine, or canine) can be an amount of about 0.005 to about 50 mg/kg body weight, about 0.01 to about 15 mg/kg body weight, about 0.1 to about 10 mg/kg body weight, about 0.5 to about 7 mg/kg body weight, about 0.005 mg/kg, about 0.01 mg/kg, about 0.05 mg/kg, about 0.1 mg/kg, about 1 mg/kg, about 5 mg/kg, about 10 mg/kg, about 20 mg/kg, about 30 mg/kg, about 40 mg/kg, about 50 mg/kg, about 80 mg/kg, about 100 mg/kg, or about 150 mg/kg. In some embodiments, the dosage can be from about 0.01 mg/kg body weight to about 150 mg/kg body weight. In some embodiments, the dosage can be from about 0.005 mg/kg body weight to about 150 mg/kg body weight. In some embodiments, an effective amount of at least one compound of the invention (e.g., Formula (I)) (which can be administered to an animal such as mammals, primates, monkeys or humans) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In some embodiments, the dosage can be from about 0.01 mg/kg body weight to about 150 mg/kg body weight. In some embodiments, the dosage can be from about 0.005 mg/kg body weight to about 150 mg/kg body weight. In some embodiments, the dosage can be about 20 mg/kg human body weight or about 100 mg/kg human body weight. In some instances, an effective amount of at least one compound of the invention (e.g., Formula (I)) (which can be administered to an animal such as mammals, rodents, mice, rabbits, feline, porcine, or canine) can be an amount of about 1 to about 1000 mg/kg body weight, about 5 to about 500 mg/kg body weight, about 10 to about 200 mg/kg body weight, about 25 to about 100 mg/kg body weight, about 1 mg/kg, about 2 mg/kg, about 5 mg/kg, about 10 mg/kg, about 25 mg/kg, about 50 mg/kg, about 100 mg/kg, about 150 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg. In some embodiments, the dosage can be from about 0.01 mg/kg body weight to about 150 mg/kg body weight. In some embodiments, the dosage can be from about 0.005 mg/kg body weight to about 150 mg/kg body weight.

"Therapeutically effective amount" means an amount effective to achieve a desired and/or beneficial effect (e.g., decreasing tumor size). A therapeutically effective amount can be administered in one or more administrations. For some purposes of this invention, a therapeutically effective amount is an amount appropriate to treat an indication (e.g., to treat cancer). By treating an indication is meant achieving any desirable effect, such as one or more of palliate, ameliorate, stabilize, reverse, slow, or delay disease (e.g., cancer) progression, increase the quality of life, or to prolong life. Such achievement can be measured by any suitable method, such as but not limited to measurement of tumor size.

In some embodiments, the treatments can also include one or more of surgical intervention, chemotherapy, radiation therapy, hormone therapies, immunotherapy, and adjuvant systematic therapies. Adjuvants may include but are not limited to chemotherapy (e.g., temozolomide), radiation therapy, antiangiogenic therapy (e.g., bevacizumab), and hormone therapies, such as administration of LHRH agonists; antiestrogens, such as tamoxifen; high-dose progestogens; aromatase inhibitors; and/or adrenalectomy. Chemotherapy can be used as a single-agent or as a combination with known or new therapies.

In some embodiments, the administration of at least one compound of the invention (e.g., Formula (I)) is an adjuvant cancer therapy or part of an adjuvant cancer therapy. Adjuvant treatments include treatments by the mechanisms disclosed herein and of cancers as disclosed herein, including, but not limited to tumors. Corresponding primary therapies can include, but are not limited to, surgery, chemotherapy, or radiation therapy. In some instances, the adjuvant treatment can be a combination of chemokine receptor antagonists with traditional chemotoxic agents or with immunotherapy that increases the specificity of treatment to the cancer and potentially limits additional systemic side effects. In still other embodiments, a compound of the invention (e.g., Formula (I)) can be used as adjuvant with other chemotherapeutic agents. The use of a compound of the invention (e.g., Formula (I)) may, in some instances, reduce the duration of the dose of both drugs and drug combinations reducing the side effects.

In some embodiments, the treatments disclosed herein can include use of other drugs (e.g., antibiotics) or therapies for treating disease. For example, antibiotics can be used to treat infections and can be combined with a compound of the invention to treat disease (e.g., infections associated with cancer). In other embodiments, intravenous immunoglobulin (IVIG) therapy can be used as part of the treatment regime (i.e., in addition to administration of the compound (s) of the invention).

In other embodiments, a method of inhibiting PFKFB4 in a cell comprising contacting the cell with an effective amount of a compound of the invention (e.g., Formula (I)) is provided. In certain embodiments, PFKFB4 is specifically inhibited by a compound of the invention. In some embodiments, "specifically inhibiting" (and other variations of inhibiting, such as "specifically inhibited") is defined as inhibiting PFKFB4 without inhibiting 6-phosphofructo-2-kinase/fructose-2,6,biphosphate 3 (PFKFB3), 6-phosphofructo-2-kinase/fructose-2,6-biphospatase 2 (PFKFB2), or 6-phosphofructo-2-kinase/fructose-2,6,biphosphate 1 (PFKFB1). Thus, in certain embodiments, a compound of the invention is a specific inhibitor of the activity of PFKFB4. In some aspects, a compound of the invention inhibits the activity of PFKFB4 by at least about 25%, about 30%, about 35%, about 40%, about 45%, about 50%, about 55%, about 60%, about 65%, about 70%, about 75%, about 80%, about 85%, about 90%, about 95% about 99%, or any value or range in between, but does not inhibit the activity of PFKFB1, PFKFB2, or PFKFB3 by more than about 20%, about 15%, about 10%, about 5%, about 2%, or about 1%.

In some embodiments of a method of inhibiting PFKFB4 in a cell comprising contacting the cell with an effective amount of a compound of the invention (e.g., Formula (I)), the cell is a mammalian cell. In certain embodiments, the cell is a cancer cell. In other embodiments, the cell is or is derived from a cell line of H460 (NSCLC), H1299 (NSCLC), H441 (NSCLC), H522 (NSCLC), DAOY and D283 (brain tumor), SKBR3 (breast), Jurkat (leukemia/hematological malignancy), B16F10 (mouse melanoma), A549 (NSCLC), MDA-MB-231 (breast cancer), LNCaP (prostatic cancer), HCT116 (colon cancer), or LLC (Lewis lung carcinoma) cell lines (e.g., obtained from ATCC).

In other embodiments, a method of inhibiting PFKFB4 in a subject in need thereof comprising administering to the subject an effective amount of a compound of the invention (e.g., Formula (I)) is provided. In certain embodiments, a compound of the invention (e.g., Formula (I)) is administered at a dosage effective for specifically inhibiting PFKFB4. In some aspects, a compound of the invention inhibits the activity of PFKFB4 by at least about 25%, about 30%, about 35%, about 40%, about 45%, about 50%, about 55%, about 60%, about 65%, about 70%, about 75%, about 80%, about 85%, about 90%, about 95% about 99%, or any value or range in between, but does not inhibit the activity of PFKFB1, PFKFB2, or PFKFB3 by more than about 20%, about 15%, about 10%, about 5%, about 2%, or about 1%. In some embodiments, the subject has cancer which can include, but is not limited to, acute lymphoblastic leukemia, astrocytoma, basal cell carcinoma, bladder cancer, bone marrow cancer, brain cancer, brain tumors (e.g., childhood brain tumors), breast cancer, chronic lymphocytic leukemia (CLL), CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, hepatocellular carcinoma, kidney cancer (e.g., renal cancer), leukemia, liver cancer, lung cancer (e.g., non-small cell lung cancer), lymphoma, melanoma (e.g., cutaneous malignant melanoma or melanoma tumorigenesis), malignancies (e.g., hematological malignancies), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In other embodiments, the subject has cancer (e.g., any of cancers disclosed herein, such as breast cancer, childhood brain tumors, hematological malignancies, leukemia, melanoma, lung cancer, colon cancer, prostate cancer, or cancerous tumors thereof).

In other embodiments, the method treats cancer including, but not limited to treating, acute lymphoblastic leukemia, astrocytoma, basal cell carcinoma, bladder cancer, bone marrow cancer, brain cancer, brain tumors (e.g., childhood brain tumors), breast cancer, chronic lymphocytic leukemia (CLL), CNS cancer (e.g., glioblastoma, glioblastoma multiforme, gliosarcoma, or astrocytoma), colon cancer, colorectal cancer (e.g., colon cancer or rectal cancer), endometrial cancer, gastric cancer, glioblastoma, glioblastoma multiforme, glioma, gliosarcoma, hepatocellular carcinoma, kidney cancer (e.g., renal cancer), leukemia, liver cancer, lung cancer (e.g., non-small cell lung cancer), lymphoma, melanoma (e.g., cutaneous malignant melanoma or melanoma tumorigenesis), malignancies (e.g., hematological malignancies), malignant nerve sheath tumors, medulloblastoma, meningioma, multiple myeloma, nasopharyngeal carcinoma, neuroblastoma, non-Hodgkin lymphoma (e.g., diffuse large B-cell lymphoma), non-small cell lung cancer, oral cancer, ovarian cancer, pancreatic cancer (e.g., pancreatic ductal adenocarcinoma), prostate cancer, rectal cancer, renal cancer, renal cell carcinoma, rhabdomyosarcoma, squamous cell carcinoma (e.g., head and neck squamous cell carcinoma), stomach cancer, thyroid cancer, uterine cancer, cancers that can result in metastasis, cancers resulting from metastasis, or cancerous tumors thereof. In other embodiments, the method treats cancer (e.g., any of cancers disclosed herein, such as breast cancer, childhood brain tumors, hematological malignancies, leukemia, melanoma, lung cancer, colon cancer, prostate cancer, or cancerous tumors thereof).

In some embodiments of a method of inhibiting PFKFB4 in a subject in need thereof comprising administering to the subject an effective amount of a compound of the invention (e.g., Formula (I)), administered orally. In other embodiments, a compound of the invention (e.g., Formula (I)) is administered intravenously.

In some embodiments of a method of inhibiting PFKFB4 in a subject comprising administering to the subject an effective amount of a compound of the invention (e.g., Formula (I)), the subject remains substantially free of signs of toxicity. In some embodiments, "substantially free of signs of toxicity" includes unsafe deviations on complete blood counts, electrolytes, hepatic and renal function, body mass, and the unsafe deviations on the gross and histological appearance of the brain, heart, lungs, liver, kidneys, and spleen due to the administration of a compound of the invention (e.g., Formula (I)) to the subject.

In other embodiments, a method of reducing proliferative capacity of a cell comprising contacting the cell with an effective amount of a compound of the invention (e.g., Formula (I)) is provided. In certain embodiments, the cell is contacted with a compound of the invention (e.g., Formula (I)) at a dosage effective for specifically inhibiting PFKFB4. In some aspects, a compound of the invention inhibits the activity of PFKFB4 by at least about 25%, about 30%, about 35%, about 40%, about 45%, about 50%, about 55%, about 60%, about 65%, about 70%, about 75%, about 80%, about 85%, about 90%, about 95% about 99%, or any value or range in between, but does not inhibit the activity of PFKFB1, PFKFB2, or PFKFB3 by more than about 20%, about 15%, about 10%, about 5%, about 2%, or about 1%.

In some embodiments of a method of reducing proliferative capacity of a cell comprising contacting the cell with an effective amount of a compound of the invention (e.g., Formula (I)), the cell is a mammalian cell. In certain embodiments, the cell is a cancer cell. In other embodiments, the cell is or is derived from a cell line of H460 (NSCLC), H1299 (NSCLC), H441 (NSCLC), H522 (NSCLC), DAOY and D283 (brain tumor), SKBR3 (breast), Jurkat (leukemia/hematological malignancy), B16F10 (mouse melanoma), A549 (NSCLC), MDA-MB-231 (breast cancer), LNCaP (prostatic cancer), HCT116 (colon cancer), or LLC (Lewis lung carcinoma) cell lines.

In other embodiments, a method of reducing fructose-2,6-bisphosphate (F2,6BP) in a cell comprising contacting the cell with an effective amount of a compound of the invention (e.g., Formula (I)) is provided. In some embodiments, the cell is a mammalian cell. In certain embodiments, the cell is a cancer cell.

Methods for Preparing Compounds of Formula (I)

Some embodiments of the present invention include methods for the preparation of compounds of Formula (I). The compounds of Formula (I) can be prepared using any suitable method or they can be purchased, if available. In certain embodiments, a compound of Formula (I) can be prepared comprising the step of reacting a compound of Formula (II) with a compound of Formula (III) to result in Formula (IV), which is later made into Formula (I) (e.g., using one or more synthetic steps).

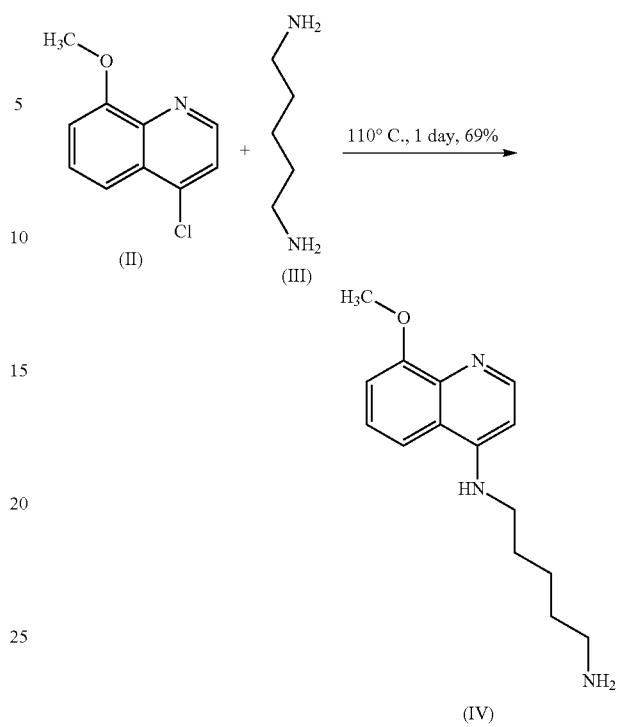

Formula (II) can be prepared using any suitable method or can be purchased if available. For example, Formula (II) can be prepared using a modified literature procedure (GHOSH et al., "Discovery of 4-(4-(2-((5-Hydroxy-1,2,3,4-tetrahydronaphthalen-2-yl)(propyl)amino)ethyl)piperazin-1-yl) quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease." J. Med. Chem. (2010) Vol. 53, pp. 2114-2125, which is herein incorporated by reference in its entirety). Formula (III) can be prepared using any suitable method or can be purchased where available.

In some embodiments, Formula (II) can be reacted with Formula (III) under the following conditions: Formula (II) and Formula (III) can be in a mixture. The mixture can be heated at a certain temperature (e.g., about 60° C., about 110° C., or about 160° C.) for a certain amount of time (e.g., about 2 hours, about 12 hours, about 24 hours, about 36 hours, about 48 hours, or about 120 hours). In other embodiments, the reaction can optionally be stopped (e.g., by pouring into cold water or ice water). Formula (IV) can optionally be recovered (e.g., extraction, chromatography, crystallization, filtration, or a combination thereof).

In some embodiments, a solution of about 1.25 g (about 6.46 mmol) of Formula (II) in about 2.0 mL of 1,5-diaminopentane (Formula (III)) can be stirred at about 110° C. for about 24 hours. In some embodiments, after cooling to about room temperature, the solution can be poured into about 150 mL (e.g., or about 5 mL or about 50 mL or about 150 mL or about 200 mL or about 300 ml or about 1000 mL) of water (e.g., cold or ice water) and then extracted (e.g., extracted one time, two times, three times, four times, five times, or ten times) with about 150-mL portions (e.g., or about 5 mL, about 50 mL, about 100 mL, about 150 mL, about 200 mL, or about 500 mL portions) of a solvent (e.g., $CH_2Cl_2$). The combined organic layers can optionally be washed (e.g., with water and brine), dried (e.g., with Na$_2$SO$_4$), concentrated (e.g., in vacuo), or a combination thereof, to provide a solid of Formula (IV). In some embodiments, the solid can optionally be recovered; for example, the solid can be chromatographed over silica gel (eluted with CH$_2$Cl$_2$→about 50% MeOH) to afford a solid (e.g., tan solid) of Formula (IV). In other embodiments, the solid can be recovered; for example, the solid can be purified by being partially dissolved in ethyl acetate, sonicated for about 5 mins and/or collected by filtration to afford semi-pure product that is suitable for further use. Formula (IV) can then optionally be further recovered using any suitable method (e.g., extraction, chromatography, crystallization, filtration, or a combination thereof) or using one or a combination of methods discussed above.

In some embodiments, Formula (IV) can be reacted with Formula (V) to provide Formula (I). Formula (IV) can be prepared using any suitable method (e.g., such as but not limited to those disclosed herein) or can be purchased if available. Formula (V) can be prepared using any suitable method or can be purchased if available. In some embodiments, Formula (IV) can be reacted with Formula (V) to provide Formula (I) under the following conditions: Formula (V) and Formula (VI) can be in a mixture comprising a solvent (e.g., ethanol) and kept at a certain temperature (e.g., about room temperature, such as about 25° C.) for a certain amount of time (e.g., about 15 hours). Formula (I) can then optionally be recovered using any suitable method.

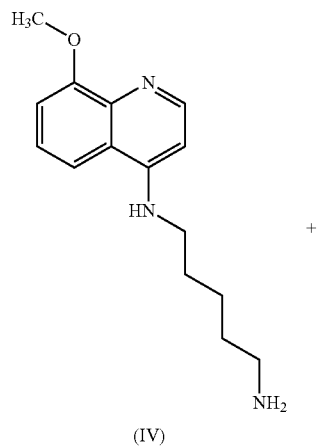

(IV)

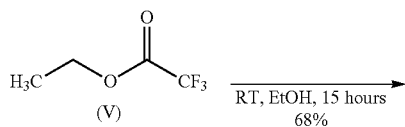

(V)

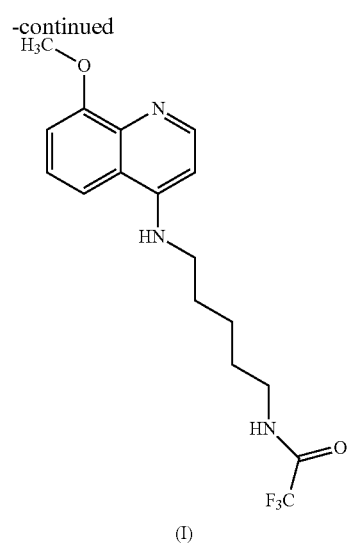

(I)

Formula (V) (e.g., about 0.6 mL or about 660 mg or about 4.7 mmol) can be added to Formula (IV) (e.g., 1.1 g or about 4.24 mmol) in about 40 mL of a solvent (e.g., anhydrous ethanol or ethanol). The resulting solution can be stirred at about room temperature (or, e.g., from about 15° C. to about 25° C.) for about 15 hours (or, e.g., from about 2 hours to about 100 hours) to provide Formula (I). The mixture can optionally be concentrated (e.g., in vacuo). Formula (I) can then optionally be recovered (e.g., extraction, chromatography, crystallization, filtration, or a combination thereof). For example, the product can be chromatographed over silica gel (eluted with CH$_2$Cl$_2$→about 35% MeOH) to afford recovered Formula (I) (e.g., as a light grey, crystalline solid).

In some embodiments, Formula (I) (or any other formula recited above) can be recovered. Recovery can occur using any suitable method including but not limited to HPLC (e.g., reverse phase), LC, extraction, drying, precipitation, centrifugation, column chromatography (e.g., size exclusion chromatography or ion exchange chromatography), use of silica gel, or combinations thereof.

In some embodiments, a method for the preparation of a compound of Formula (I) can comprise one or more of the above-mentioned steps. In certain embodiments, a method for preparing a compound of Formula (I) comprises (a) reacting a compound of Formula (II) with a compound of Formula (III) to result in a mixture comprising a compound of Formula (IV);

(b) reacting a compound of Formula (IV) with a compound of Formula (V); and;

(c) recovering Formula (I).

The presently-disclosed subject matter is further illustrated by the following specific but non-limiting examples. The following examples may include compilations of data that are representative of data gathered at various times during the course of development and experimentation related to the present invention.

EXAMPLES

Example Set A—Synthetic Methods and Compound Characterization

All commercially purchased chemicals and solvents were used without further purification. All reactions were conducted under a nitrogen atmosphere in flame dried glassware. Reactions were monitored by thin-layer chromatography (TLC) on silica gel plates (Analtech, Uniplates GHLF, 0.25 mm with UV254) and were visualized with UV light (254 nm and 360 nm) or potassium permanganate stain. Isolated compounds were purified via flash chromatography on a Teledyne Isco Combiflash $R_f$ with prepacked silica gel columns eluted with an optimal gradient as described. All NMR spectra were recorded on an Agilent 400 MR spectrometer equipped with an OneProbe at 400 MHz for $^1$H, 376 MHz for $^{19}$F and 100 MHz for $^{13}$C. Chemical shifts were recorded as δ values in parts per million (ppm) at 25° C. and either tetramethylsilane (TMS) or residue solvent was used as an internal standard. Coupling constants are reported in hertz (Hz) and splitting patterns are designated as s, singlet; d, doublet; t, triplet; q, quartet; m, multiplet. Analytical purity was determined by reverse-phase high-performance liquid chromatography (RP-HPLC) on an Agilent 1260 infinity equipped with a diode array (160-450 nm). The instrument was equipped with an Agilent Zobrax Extend C-18 column (1.8 μm, 2.1×50 mm) with mobile phase consisting of mass spectrophotometry grade water (with 0.1% formic acid and 0.1% methanol) and acetonitrile (with 0.1% formic acid). The RP-HPLC method employed a linear gradient from 5%-100% acetonitrile at 0.3 mL/min over 15 mins with 4 μL injection volume. High-resolution MS were recorded on an Agilent 6224 time-of-flight detector connected to the HPLC system that utilized electrospray ionization.

Compound I was synthesized according to the following synthetic scheme.

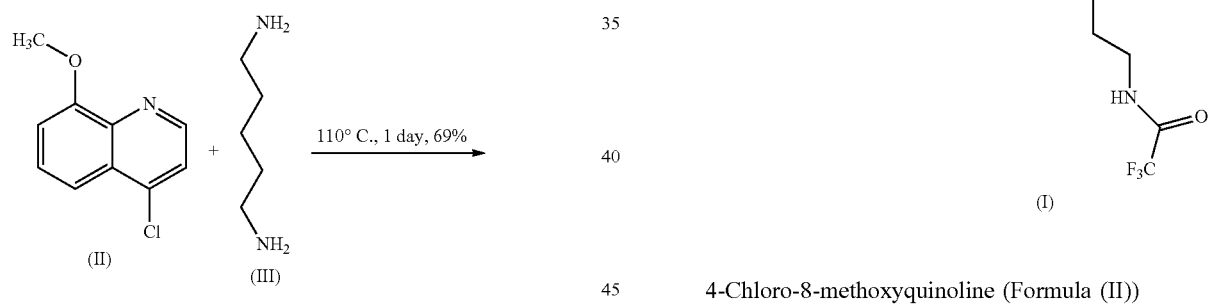

4-Chloro-8-methoxyquinoline (Formula (II))

Formula (II) was purchased (e.g., from MilliporeSigma (Order number: BB0000177-1G)) or prepared from 2-methoxyaniline using a modified literature procedure (GHOSH et al., "Discovery of 4-(4-(2-((5-Hydroxy-1,2,3,4-tetrahydronaphthalen-2-yl)(propyl)amino)ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease." J. Med. Chem. (2010) Vol. 53, pp. 2114-2125, which is herein incorporated by reference in its entirety).

$N^1$-(8-methoxyquinolin-4-yl)pentane-1,5-diamine (Formula (IV))

A solution of 1.25 g (6.46 mmol) of Formula (II) in 2.0 mL of 1,5-diaminopentane (Formula (III); purchased from TCI America (Order number: D0108)) was stirred at 110° C. for 24 hours. After cooling to room temperature, the solution was poured into 150 mL of ice water and then extracted three times with 150-mL portions of CH$_2$Cl$_2$. The combined organic layers were washed with water and brine, dried ($Na_2SO_4$) and concentrated in vacuo. The solid was chromatographed over silica gel (eluted with $CH_2Cl_2 \rightarrow 50\%$ MeOH) to afford 1.15 g (69%) of Formula (IV) as a tan solid. Alternatively or additionally, the solid can be purified by partially dissolving in ethyl acetate, sonicating for 5 mins and/or collecting the solid by filtration to afford semi pure product that is suitable for further use. $^1$H NMR (400 MHz, DMSO-$d_6$) δ 8.32 (d, J=5.2 Hz, 1H), 7.73 (dd, J=8.4, 0.8 Hz, 1H), 7.30 (td, J=8.4, 0.8 Hz, 1H), 7.05 (dd, J=8.0, 0.8 Hz, 1H), 6.99 (s, br, 1H), 6.44 (d, J=5.2 Hz, 1H), 3.88 (s, 3H), 3.23 (t, J=6.8 Hz, 2H), 2.54 (t, J=6.4 Hz, 2H), 1.65 (quint, J=7.2 Hz, 2H), 1.47-1.33 (m, 4H); $^{13}$C NMR (100.5 MHz, DMSO-$d_6$) δ 155.4, 149.7, 149.1, 140.2, 123.6, 119.6, 113.2, 108.0, 98.6, 55.5, 42.5, 41.5, 32.9, 27.8, 24.1. ESI-HRMS m/z: [M+H]$^+$ calcd for $C_{15}H_{22}N_3O$ 260.1757, found 260.1758.

2,2,2-trifluoro-N-(5-((8-methoxyquinolin-4-yl)amino)pentyl)acetamide (Formula (I))

To a solution of 1.1 g (4.24 mmol) of Formula (IV) in 40 mL of anhydrous ethanol was added 0.6 mL (660 mg, 4.7 mmol) of ethyl trifluoroacetate (Formula (V); purchased from Oakwood Chemical (Order number: 001179)). The resulting solution stirred for 15 hours at room temperature and then was concentrated in vacuo. The product was chromatographed over silica gel (eluted with $CH_2Cl_2 \rightarrow 35\%$ MeOH) to afford 1.03 g (68%) of Formula (I) as a light grey, crystalline solid. $^1$H NMR (400 MHz, CDCl$_3$) δ 9.42 (t, J=5.2 Hz, 1H), 8.32 (d, J=6.0 Hz, 1H), 7.78 (dd, J=8.8, 1.2 Hz, 1H), 7.35 (t, J=8.0 Hz, 1H), 7.33 (s, br, 1H), 7.12 (d, J=7.2 Hz, 1H), 6.52 (d, J=5.6 Hz, 1H), 3.91 (s, 3H), 3.28 (q, J=6.4 Hz, 2H), 3.20 (q, J=6.4 Hz, 2H), 1.68 (quint, J=7.2 Hz, 2H), 1.55 (quint, J=7.2 Hz, 2H), 1.43-1.33 (m, 2H); $^{13}$C NMR (100.5 MHz, DMSO-$d_6$) δ 156.2 (q, J=35.9 Hz), 154.4, 150.6, 147.8, 138.4, 124.1, 119.3, 116.0 (q, J=288.2 Hz), 113.3, 108.7, 98.7, 55.7, 54.9, 42.4, 28.4, 27.4, 23.8; $^{19}$F NMR (376 MHz, DMSO-$d_6$) δ −74.4 (s, 3F); ESI-HRMS m/z: [M+H]$^+$ calcd for $C_{17}H_{21}F_3N_3O_2$ 356.1580, found 356.1570.

Example Set B—Biological Characterization

Inhibiting PFKFB4 Activity by Formula (I) (Also Referred to as FBR1-12):

The efficacy of the compound Formula (I) in inhibiting the activity of the PFKFB4 enzyme was tested by examination of the effect of Formula (I) on the kinase activity of recombinant PFKFB4 enzyme in the ADP-Glo assay. FIG. 1 shows that Formula (I) inhibited the kinase activity of the PFKFB4 enzyme, and thereby indicating its ability to decrease the production of F26BP by PFKFB4.

Method:

The efficacy of Formula (I) in inhibition of the kinase activity of the PFKFB4 enzyme was examined by exposing recombinant human PFKFB4 protein to Formula (I) in the ADP-Glo kinase assay (Promega) which measures ADP formed through a kinase reaction. Briefly, recombinant protein, ATP, substrate and Formula (I) were incubated together for the kinase reaction followed by the addition of ADP-Glo reagent, used to terminate the kinase reaction. Lastly, a kinase detection reagent was added to convert the newly formed ADP to ATP which was measured by a luciferase reaction. Data are shown in FIG. 1 as the decrease in luminescence caused by Formula (I) relative to DMSO.

Figure 2:
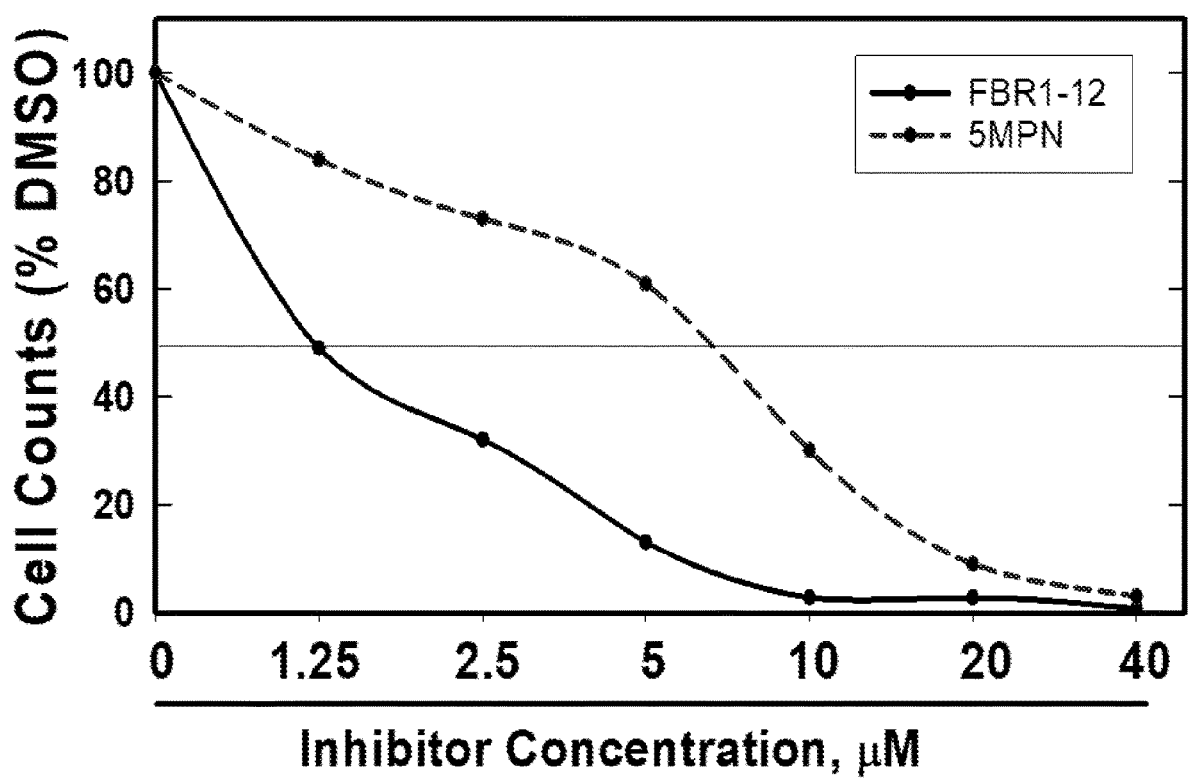
FIG. 2: Decrease in cell proliferation by Formula (I).

Decrease in Cell Proliferation by Formula (I) (Also Referred to as FBR1-12):

The effect of increasing concentrations of Formula (I) on the proliferation of human cancer cells was examined in vitro. FIG. 2 shows that Formula (I) decreases the proliferation of human cancer cell lines in vitro with higher potency than SMPN (5-[(8-methoxyquinolin-4-yl)amino]pentyl nitrate). Data in FIG. 2 are shown as the decrease in cell counts relative to the DMSO (vehicle) control.

Method: Cells were plated in 24 well plates and exposed to increasing concentrations of Formula (I). DMSO was used as a vehicle. After 24, 48 and 72 hours of exposure, cells were detached, and viable cells were counted by Trypan blue exclusion (representative counts at 48 hours shown).

Figure 3:
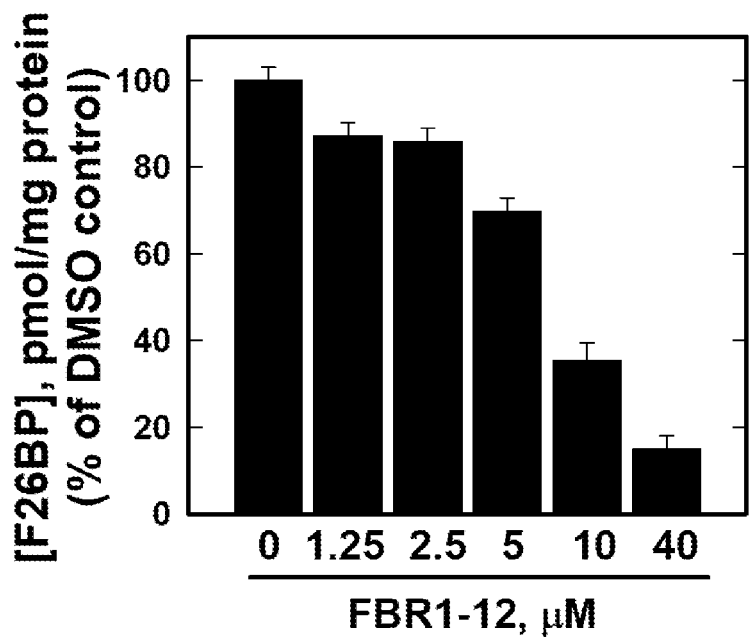
FIG. 3: Decrease in fructose-2,6-bisphosphate (F26BP) in cells by Formula (I).
Figure 3:
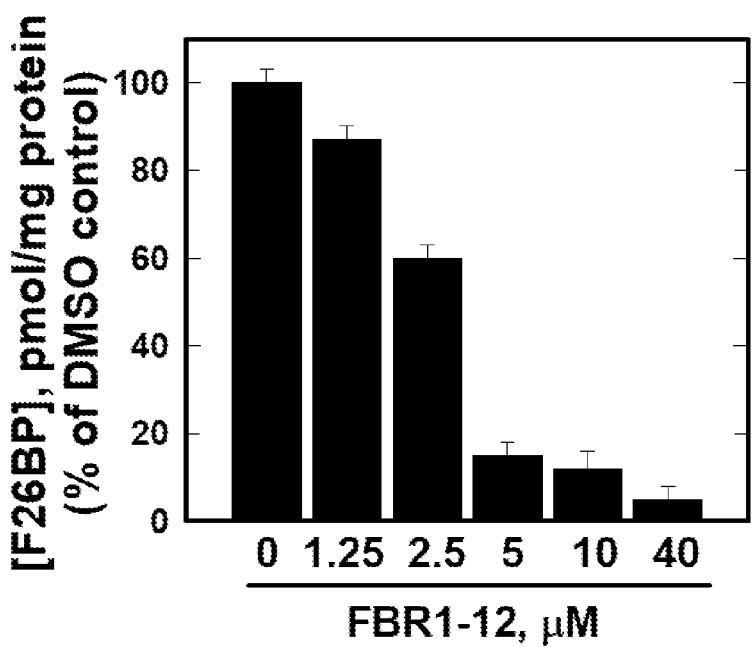

Decrease in Fructose-2,6-Bisphosphate (F26BP) in Cells by Formula (I) (Also Referred to as FBR1-12):

The ability of Formula (I) to inhibit the activity of the PFKFB4 enzyme in cells was measured by examining the effect of the inhibitor on the levels of the product of the PFKFB4 enzyme, fructose-2,6-bisphosphate (F26BP). FIG. 3A and FIG. 3B (two independently run experiments) show that Formula (I) has a dose-dependent decrease in F26BP in cancer cells. Data in FIG. 3 are shown as the concentration of intracellular F26BP normalized to cellular protein concentration.

Method:

In order to measure F26BP, cells were exposed to increasing concentrations of Formula (I) and were harvested, washed with PBS, lysed in NaOH/Tris acetate by heating at 80° C. and lysates neutralized to pH 7.2. F26BP content was measured using a coupled enzyme reaction following the method of Van Schaftingen (VAN SCHAFTINGEN et al, "A kinetic study of pyrophosphate: fructose-6-phosphate phosphotransferase from potato tubers. Application to a microassay of fructose 2,6-bisphosphate" Eur J Biochem. (1982) Vol. 129, No. 1, pp. 191-195), which is herein incorporated by reference in its entirety. The F26BP concentration was normalized to total cellular protein measured by the bicinchoninic acid assay (BCA, Thermo Scientific).

Figure 4:
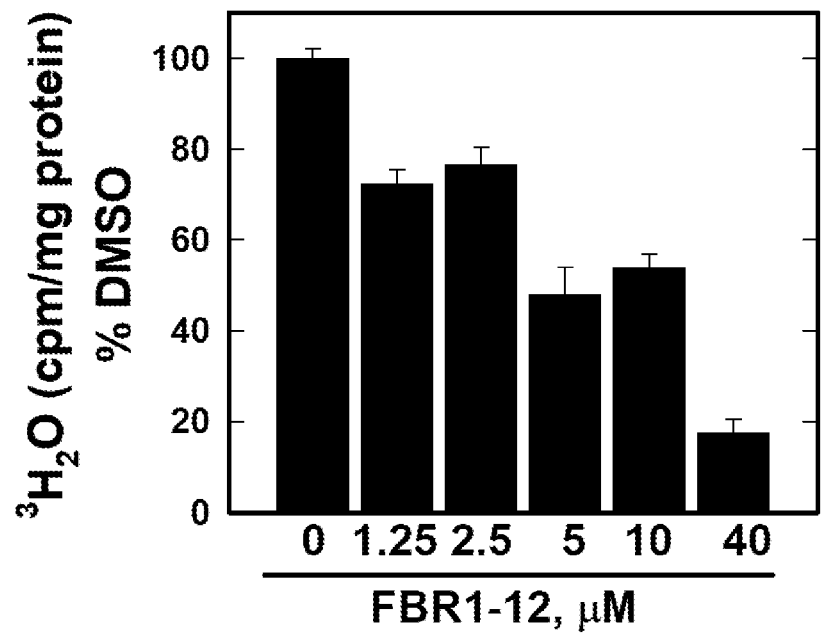
FIG. 4: Decrease in glycolysis in cells by Formula (I).
Figure 4:
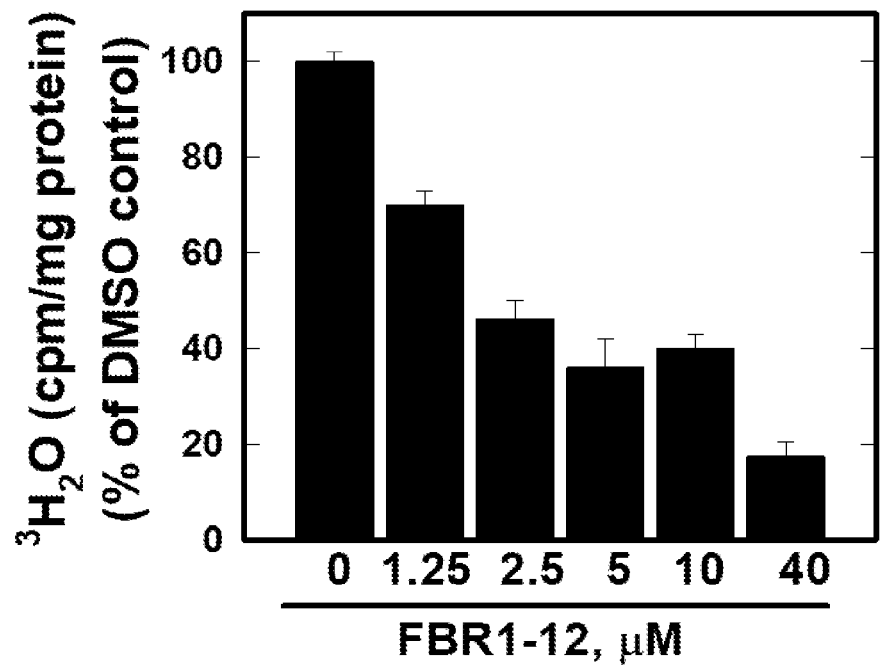

Decrease in Glycolysis in Cells by Formula (I) (Also Referred to as FBR1-12):

The effect of Formula (I) on the glycolytic pathway was examined to determine the ability of this inhibitor to decrease glycolysis secondary to its effect on PFKFB4-driven F26BP production. PFKFB4 produces F26BP which activates a rate-limiting enzyme of the glycolytic pathway, 6-phosphofructo-2-kinase (PFK-1). FIG. 4A and FIG. 4B (two independently run experiments) show that Formula (I) caused a dose-dependent decrease in glycolysis in cancer cells measured by the production of tritiated $H_2O$ ($^3H_2O$) in glycolysis through the enzyme enolase from 5-[$^3$H]glucose added to the medium. Data in FIG. 4A and FIG. 4B are shown as the production of $^3H_2O$ by Formula (I) relative to DMSO and normalized to protein concentration.

Method: To examine glycolysis, cells growing in 6-well plates were incubated in 500 μl of complete medium containing 1 μCi of 54411 glucose per well for 60 min in 5% $CO_2$ at 37° C. The medium was then collected and centrifuged to pellet any suspended cells. To separate the $^3H_2O$ formed via glycolysis from the 5-[$^3$H]glucose added to the medium, an evaporation technique in a sealed system was utilized. Briefly, 150 μl aliquots of medium were added to open tubes that were placed upright inside scintillation vials containing 1 ml of $H_2O$. The scintillation vials were sealed, and the $^3H_2O$ produced by glycolysis through enolase and released to the medium was allowed to equilibrate with the H$_2$O in the outer vial for 48 h at 37° C. The amounts of $^3$H$_2$O that had diffused into the surrounding H$_2$O was measured on a Tri-Carb 2910 liquid scintillation analyzer (Perkin Elmer) and compared with $^3$H$_2$O and 5-[$^3$H]glucose standards. Protein concentration was determined using the BCA assay and counts were normalized to protein concentration (previously described in CHESNEY et al., "Fructose-2,6-bisphosphate synthesis by 6-phosphofructo-2-kinase/fructose-2,6-bisphosphatase 4 (PFKFB4) is required for the glycolytic response to hypoxia and tumor growth" Oncotarget (2014) Vol. 5, No. 16, pp. 6670-6686, which is herein incorporated by reference in its entirety).

Figure 5:
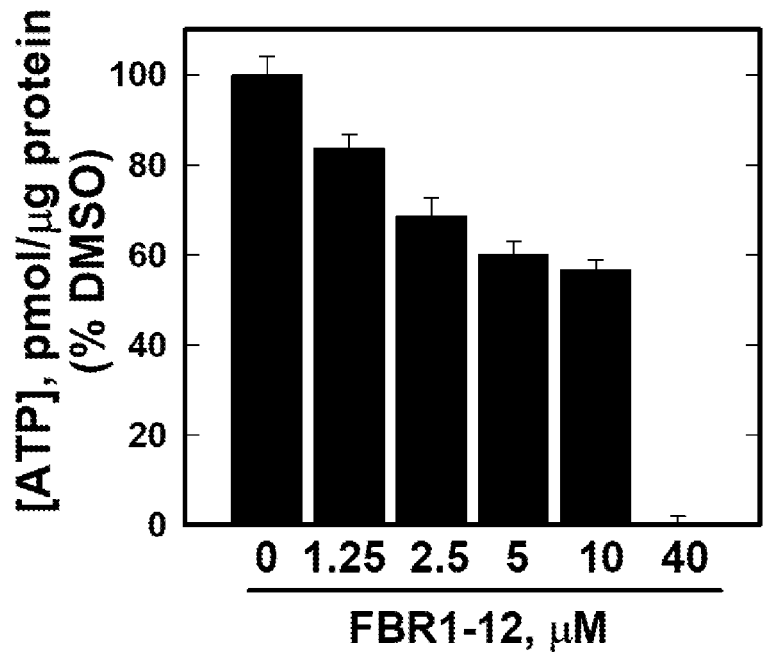
FIG. 5: Decrease in ATP production in cells by Formula (I).
Figure 5:
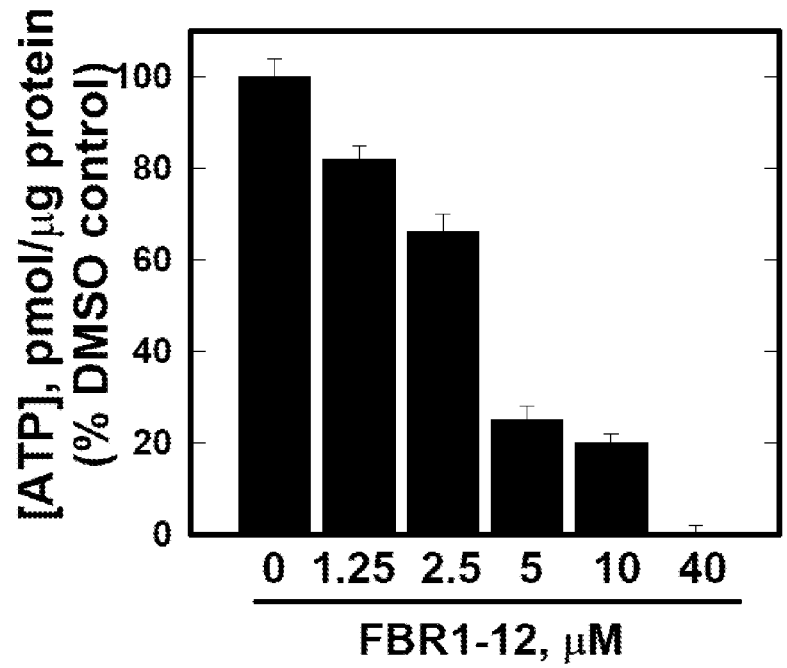

Decrease in ATP Production in Cells by Formula (I) (Also Referred to as FBR1-12):

The effect of Formula (I) on the production of ATP was examined as a measure of its effect on energy production by the glycolytic pathway. FIG. 5A and FIG. 5B (two independently run experiments) show that Formula (I) caused a dose-dependent decrease in the production of ATP by cancer cells.

Method:

To measure ATP, cells were washed (while still adherent) with cold PBS, lysed with Passive Lysis Buffer (Molecular Probes, Invitrogen) added directly to the plates, and immediately harvested by scraping. The lysates were flash frozen (to −80° C.) and thawed (to 37° C.) once to accomplish complete lysis and then centrifuged to clear the lysates. Intracellular ATP levels were determined using a bioluminescence assay (Molecular Probes), utilizing luciferase and its substrate, D-luciferin and ATP values were calculated using an ATP standard curve. The ATP concentration was normalized to protein concentration that was estimated using the BCA assay.

Figure 6:
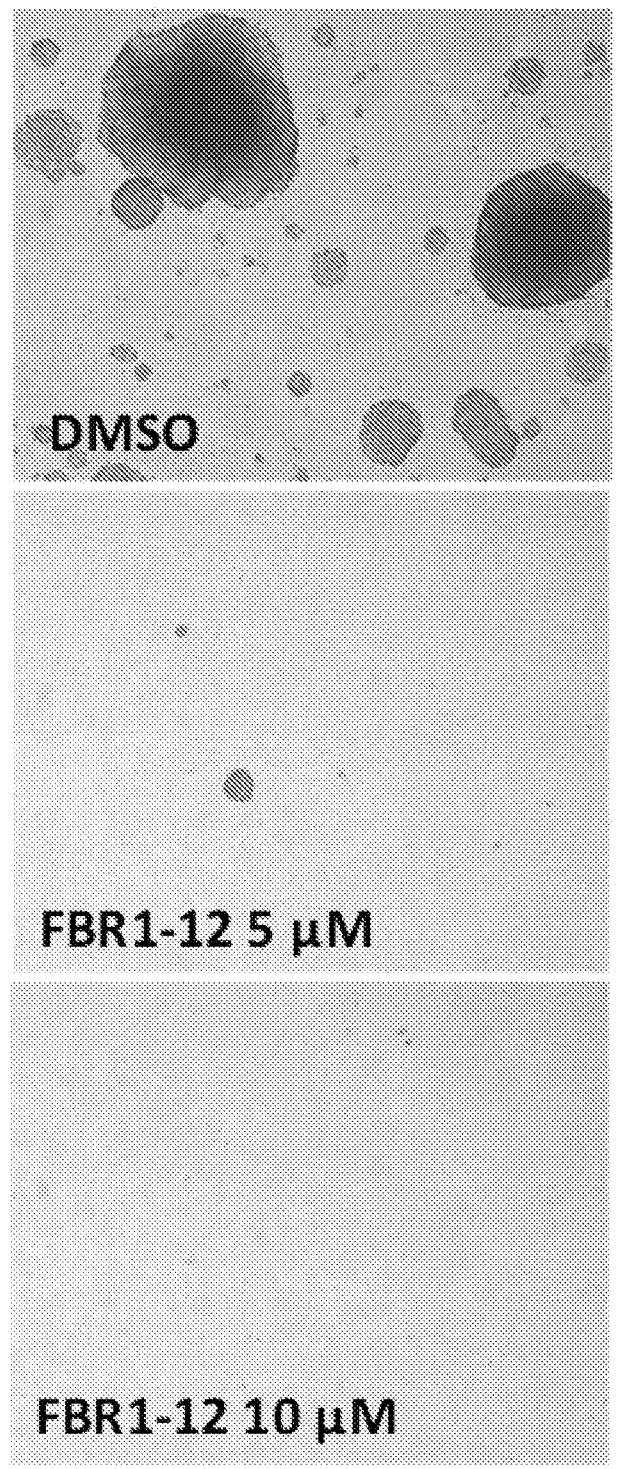
FIG. 6: Decrease in anchorage independent growth in cells by Formula (I).
Figure 6:
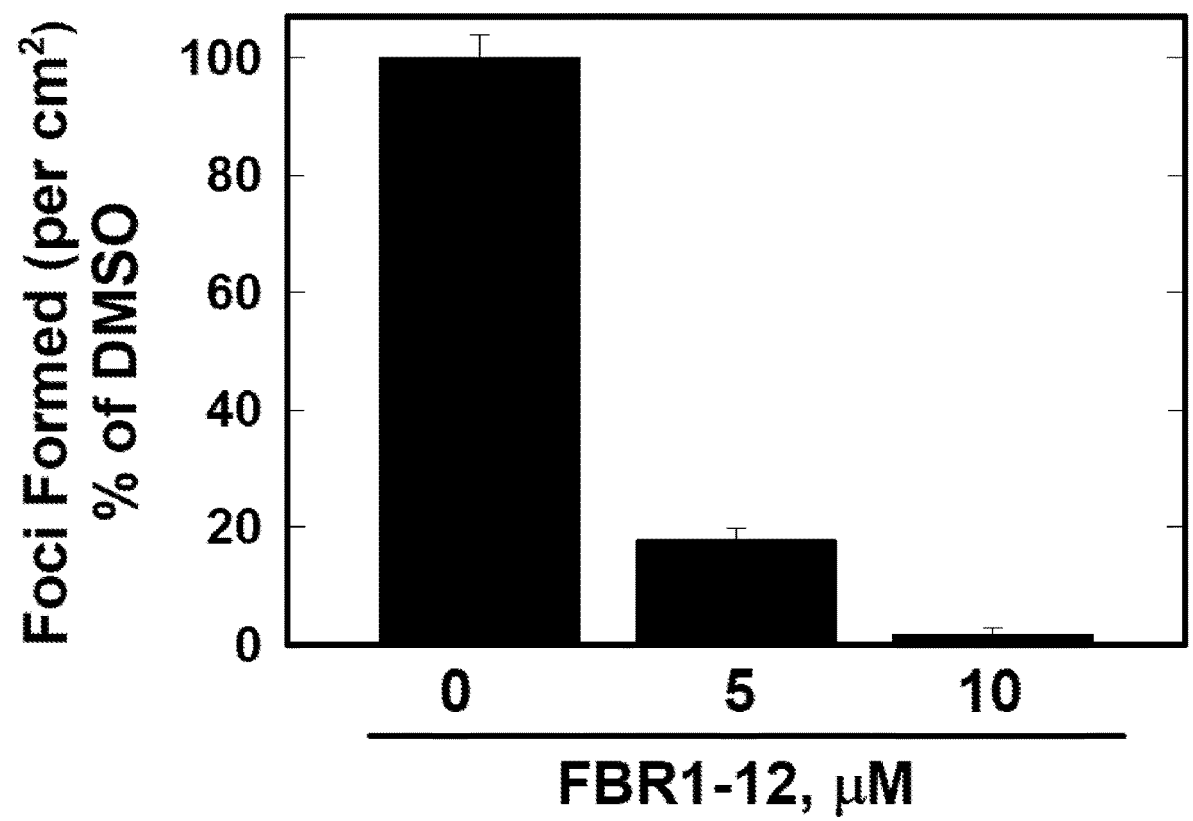

Decrease in Anchorage Independent Growth in Cells by Formula (I) (Also Referred to as FBR1-12):

We examined the ability of Formula (I) to inhibit the anchorage independent growth of cancer cells in vitro as colonies in soft agar. Anchorage independent growth is an in-vitro surrogate for tumor growth and we found that Formula (I) inhibited the growth of cancer cells as soft agar colonies. Representative images are shown in FIG. 6A, and colonies formed were enumerated. The number of colonies formed in the presence of Formula (I) was compared with those formed in the presence of the vehicle, DMSO (FIG. 6B).

Method:

Cancer cells were plated in soft agar and the effects of increasing concentrations of Formula (I) on anchorage independent growth was examined Briefly, a feeder layer of 0.6% agarose (Agar Noble, Becton Dickinson) in RPMI with 10% fetal bovine serum was plated in 6 cm plates containing vehicle (DMSO) or increasing concentrations of Formula (I). 1×10$^4$ cells were re-suspended in 0.3% agarose in RPMI/10% serum containing DMSO or increasing concentrations of Formula (I) and plated on top of the feeder layer. Cells were allowed to grow at 37° C. in 5% CO$_2$ and agarose-containing media with DMSO+/−Formula (I) was replenished every 5 days until colonies became visible. Colonies were stained with MTT [3-(4,5-dimethylthiazol-2-yl)-2,5-diphenyl tetrazolium bromide] and counted in four random 1 cm$^2$ areas per plate under 40× magnification and enumerated.

Figure 7:
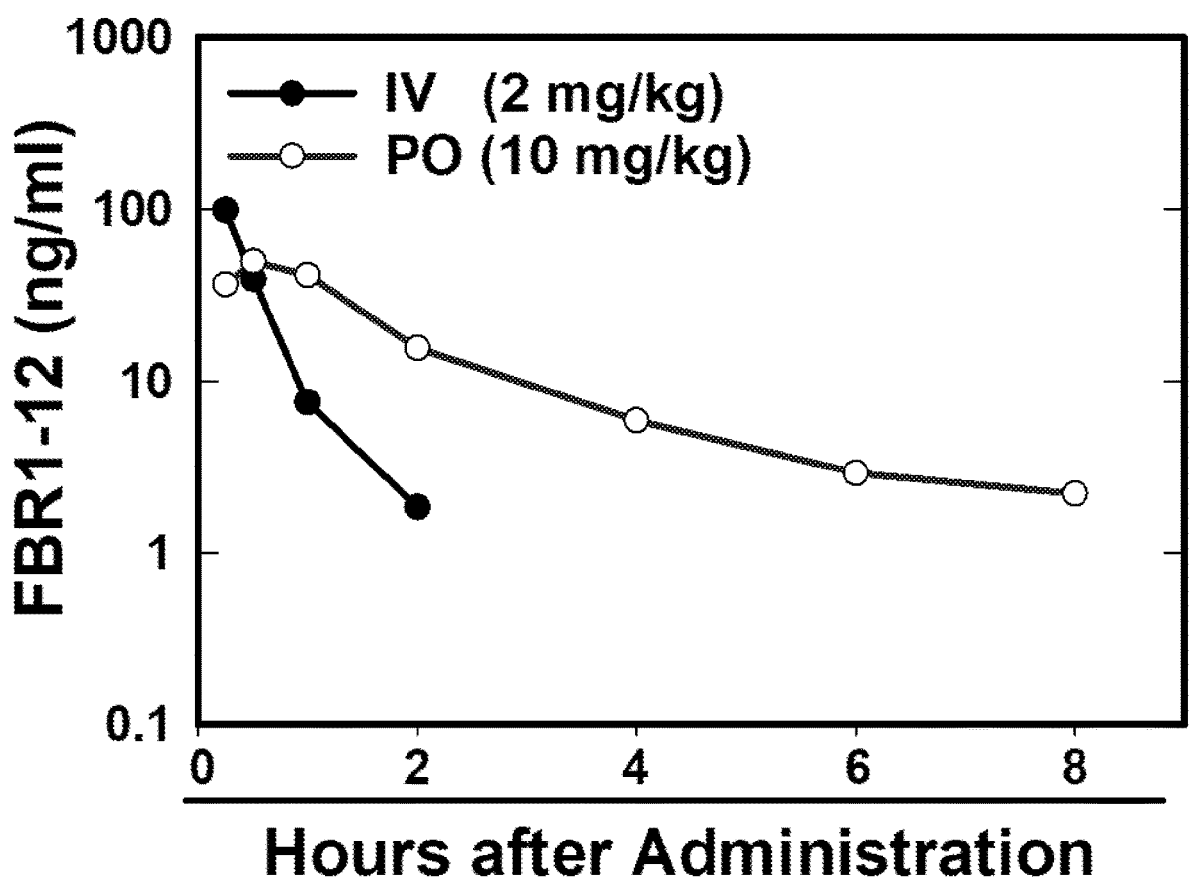
FIG. 7: Pharmacokinetic profile of Formula (I).

Pharmacokinetic Profile of Formula (I) (Also Referred to as FBR1-12):

The pharmacokinetic profile of Formula (I) was determined in mice following IV and oral administration of Formula (I) (FIG. 7).

Method: The pharmacokinetic profile of Formula (I) was determined in male CD-1 mice dosed orally and IV with Formula (I)/Nine time points (n=3 per time point) were used to determine indicated PK parameters calculated using WinNonLin v5.0. Plasma samples were extracted using acetonitrile and analyzed by LC/MS-MS using a Waters XSELECT CSH C18 2.5 micron 50×2.1 mm column eluted with a biphasic mobile phase (0.1% formic acid in acetonitrile and water).

Figure 8:
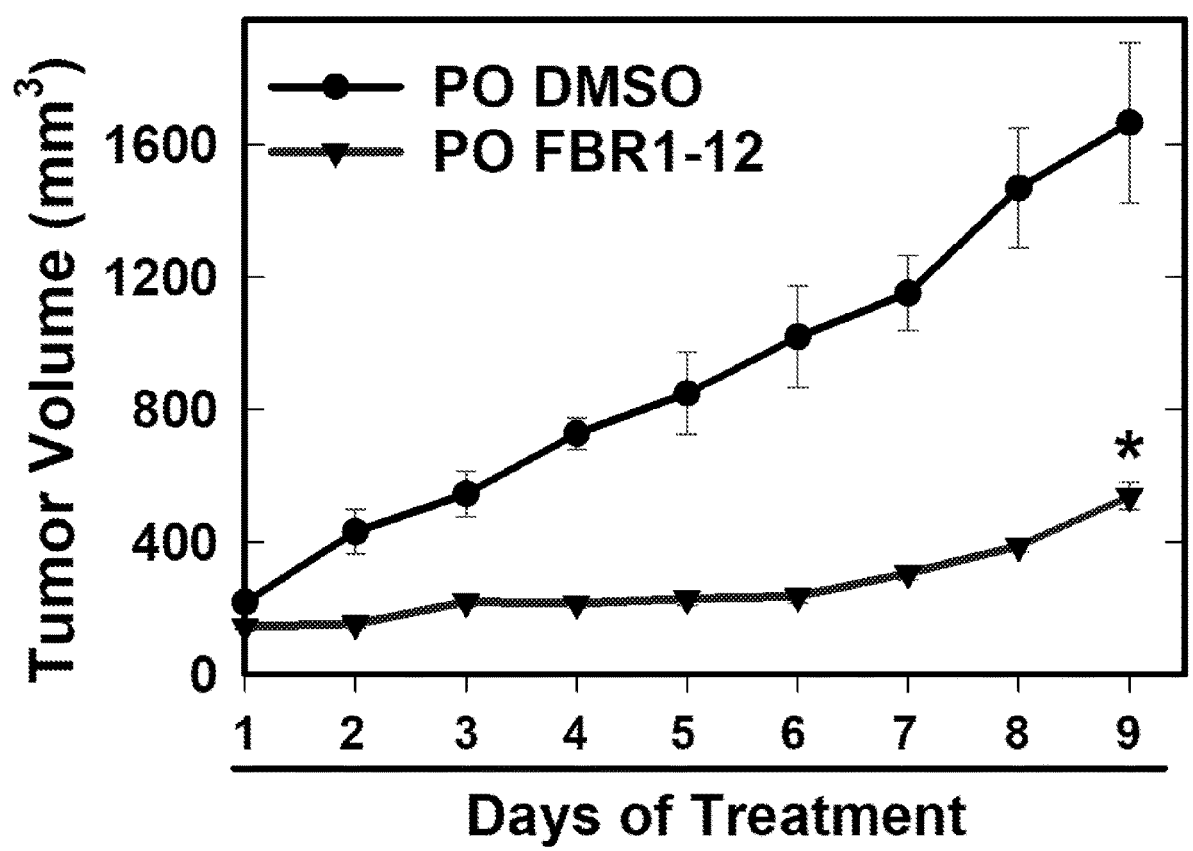
FIG. 8: Formula (I) decreases growth of tumors in vivo.

Formula (I) (Also Referred to as FBR1-12) Decreased the Growth of Tumors In Vivo:

The efficacy of Formula (I) in decreasing the growth of tumors in vivo was examined Mice were implanted with Lewis lung carcinoma cells and after tumors were noted, dosed daily with DMSO±Formula (I) by gavage and tumor growth followed. FIG. 8 shows that oral Formula (I) administration decreased established tumor growth in a syngeneic mouse tumor model. Data shown as mean±SEM for each timepoint.

Method:

C57BL/6 mice (Charles River) were implanted with 1×10$^6$ Lewis lung carcinoma cells subcutaneously and, after tumors developed, were followed by caliper measurements daily to quantify tumor mass using the formula: tumor mass=(length×width$^2$)/2. When tumors were ~150-200 mg, mice were randomized to daily oral DMSO±Formula (I) (n=10/group) at 40 mg/kg in 50 μL DMSO and tumor growth followed×9 days. (* signifies statistical significance)

Figure 9:
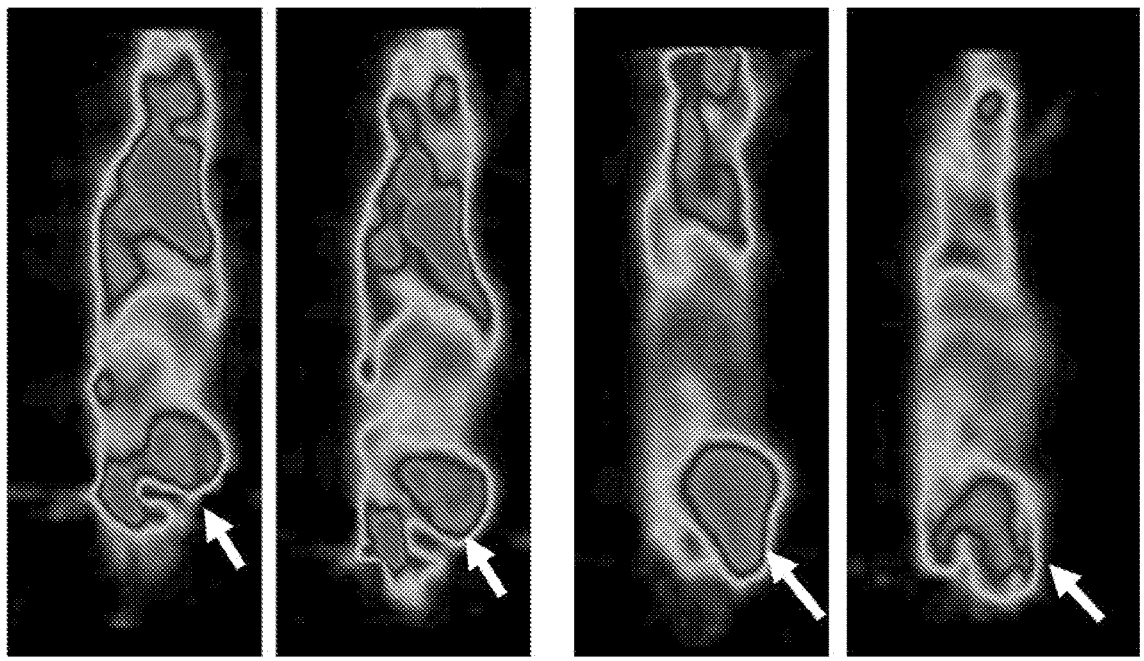
FIG. 9: Formula (I) decreases glucose uptake in tumors in vivo.
Figure 9:
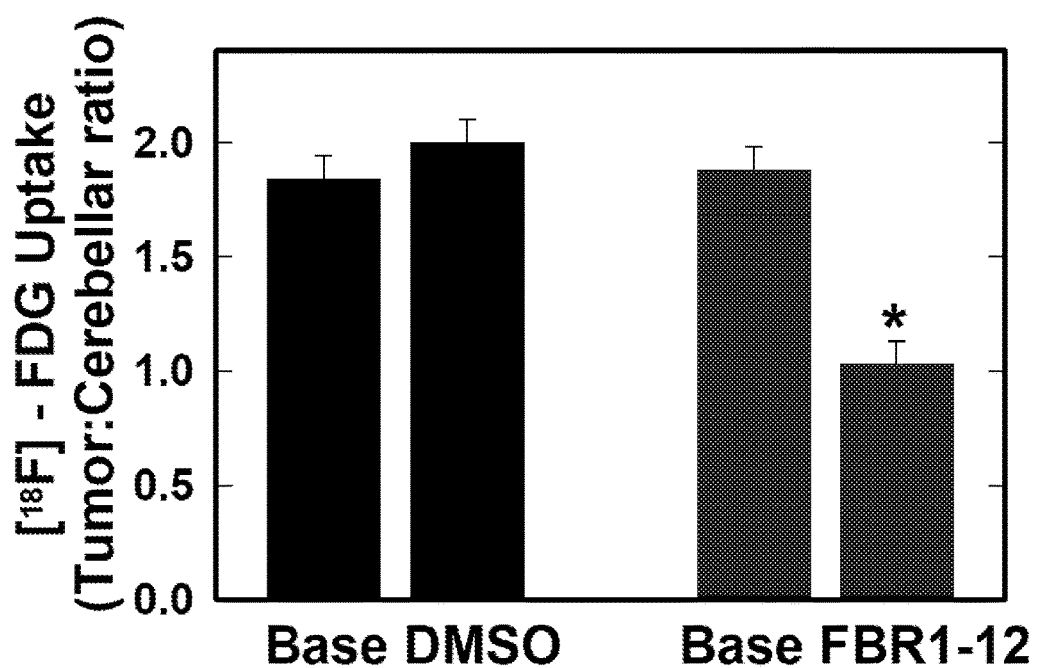

Formula (I) (Also Referred to as FBR1-12) Decreased Tumor Glucose Uptake in Tumors In Vivo:

The efficacy of Formula (I) to decrease tumor glucose uptake was examined by positron emission tomography (PET) following $^{18}$F-fluoro-2-deoxy-glucose (FDG) injection. FIG. 9 shows that Formula (I) administration caused a decrease in tumor FDG uptake compared with vehicle.

Method: FDG-PET was conducted on tumor-bearing mice to determine acute effects of Formula (I) on glucose uptake. C57BL/6 mice (Charles River) with subcutaneous Lewis lung carcinoma tumors were injected intraperitoneally with 100 μCi of $^{18}$F-fluoro-2-deoxy-glucose under isoflurane anesthesia and subjected to a 15-minute static scan 45 minutes after tracer injection at baseline. Twenty-four hours later, the same animals were administered vehicle (DMSO) or Formula (I) (in DMSO, 40 mg/kg, PO×1), and, after 60 minutes, FDG uptake determined by PET scan. Tumor/cerebellum ROI (regions of interest) were quantified, representative sagittal cuts from mice are shown with arrows showing the tumors on the animals. (* signifies statistical significance).

The headings used in the disclosure are not meant to suggest that all disclosure relating to the heading is found within the section that starts with that heading. Disclosure for any subject may be found throughout the specification.

It is noted that terms like "preferably," "commonly," and "typically" are not used herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

As used in the disclosure, "a" or "an" means one or more than one, unless otherwise specified. As used in the claims, when used in conjunction with the word "comprising" the words "a" or "an" means one or more than one, unless otherwise specified. As used in the disclosure or claims, "another" means at least a second or more, unless otherwise specified. As used in the disclosure, the phrases "such as", "for example", and "e.g." mean "for example, but not limited to" in that the list following the term ("such as", "for example", or "e.g.") provides some examples but the list is not necessarily a fully inclusive list. The word "comprising" means that the items following the word "comprising" may include additional unrecited elements or steps; that is, "comprising" does not exclude additional unrecited steps or elements.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

Detailed descriptions of one or more embodiments are provided herein. It is to be understood, however, that the present invention may be embodied in various forms. Therefore, specific details disclosed herein (even if designated as preferred or advantageous) are not to be interpreted as limiting, but rather are to be used as an illustrative basis for the claims and as a representative basis for teaching one skilled in the art to employ the present invention in any appropriate manner Indeed, various modifications of the invention in addition to those described herein will become apparent to those skilled in the art from the foregoing description and the accompanying figures. Such modifications are intended to fall within the scope of the appended claims.

What is claimed is:

1. A compound selected from Formula (I)

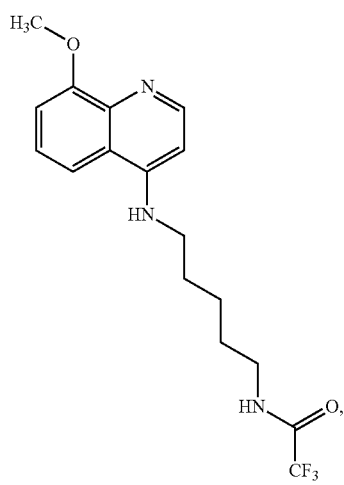

(I)

a salt of Formula (I), an optical isomer of Formula (I), a geometric isomer of Formula (I), a salt of an optical isomer of Formula (I), or a salt of a geometric isomer of Formula (I).

2. The compound of claim 1, wherein the compound is a salt of Formula (I).

3. The compound of claim 1, wherein the compound is

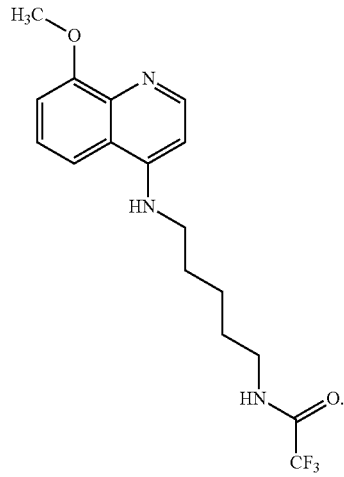 [SMILES: COc1cccc2c(NCCCCCNC(=O)C(F)(F)F)ccnc12]

4. A composition comprising the compound of claim 1.

5. The composition of claim 4, wherein the amount of the compound is from about 0.0001% to about 99%, by weight total composition.

6. The composition of claim 4, further comprising a formulary ingredient, an adjuvant, or a carrier.

7. A pharmaceutical composition comprising the compound of claim 1.

8. The pharmaceutical composition of claim 7, wherein the amount of the compound is from about 0.0001% to about 50%, by weight total composition.

9. The pharmaceutical composition of claim 7, further comprising a formulary ingredient, an adjuvant, or a carrier.

10. A method for providing an animal with a compound comprising one or more administrations of one or more compositions comprising the compound of claim 1, wherein the compositions may be the same or different if there is more than one administration.

11. The method of claim 10, wherein at least one of the one or more compositions further comprises a formulary ingredient.

12. The method of claim 10, wherein at least one of the one or more compositions comprises a pharmaceutical composition.

13. The method of claim 10, wherein at least one of the one or more administrations comprises parenteral administration, mucosal administration, intravenous administration, subcutaneous administration, topical administration, intradermal administration, oral administration, sublingual administration, intranasal administration, or intramuscular administration.

14. The method of claim 10, wherein if there is more than one administration at least one composition used for at least one administration is different from the composition of at least one other administration.

15. The method of claim 10, wherein the compound of at least one of the one or more compositions is administered to the animal in an amount of from about 0.01 mg/kg animal body weight to about 150 mg/kg animal body weight.

16. The method of claim 10, wherein the animal is a human, a rodent, or a primate.

17. A method for treating an animal for a disease, comprising one or more administrations of one or more compositions comprising the compound of claim 1, wherein (a) the compositions may be the same or different if there is more than one administration, (b) treating does not include prophylactic treatment of cancer, and (c) the disease is (i) acute lymphoblastic leukemia, astrocytoma, basal cell carcinoma, bladder cancer, brain cancer, brain tumors, breast cancer, chronic lymphocytic leukemia (CLL), colon cancer, colorectal cancer, diffuse large B-cell lymphoma, gastric cancer, glioblastoma, glioblastoma multiforme, glioma, hematological malignancies, leukemias, lung cancer, lymphoma, medulloblastoma, neuroblastoma, non-Hodgkin lymphoma, non-small cell lung cancer, pancreatic cancer, prostate cancer, and rectal cancer, (ii) metastatic cancers resulting from (i), or (iii) cancerous tumors of (i) or (ii).

18. The method of claim 17, wherein at least one of the one or more compositions further comprises a formulary ingredient.

19. The method of claim 17, wherein at least one of the one or more compositions comprises a pharmaceutical composition.

20. The method of claim 17, wherein at least one of the one or more administrations comprises parenteral administration, mucosal administration, intravenous administration, subcutaneous administration, topical administration, intradermal administration, oral administration, sublingual administration, intranasal administration, or intramuscular administration.

21. The method of claim 17, wherein if there is more than one administration at least one composition used for at least one administration is different from the composition of at least one other administration.

22. The method of claim 17, wherein the compound of at least one of the one or more compositions is administered to the animal in an amount of from about 0.005 mg/kg animal body weight to about 150 mg /kg animal body weight.

23. The method of claim 17, wherein the animal is a human, a rodent, or a primate.

24. The method of claim 17, wherein the animal is in need of the treatment.

25. The method of claim 17, wherein the method is for treating (i) non-small cell lung cancer, colorectal cancer, prostate cancer, breast cancer, pancreatic cancer, lymphoma, or medulloblastoma or (ii) cancerous tumors of (i).

26. The method of claim 17, wherein the method is for treating (i) non-small cell lung cancer, colorectal cancer, prostate cancer, or breast cancer or (ii) cancerous tumors of (i).

27. The method of claim 17, wherein the method is for treating non-small cell lung cancer or cancerous tumors thereof.

28. A method of inhibiting PFKFB4 in a cell, the method comprising contacting the cell with the compound of claim 1.

29. The method of claim 28, wherein PFKFB4 is specifically inhibited.

30. The method of claim 28, wherein the cell is a mammalian cell.

31. The method of claim 28, wherein the cell is a cancer cell.

32. The method of claim 28, wherein the cell is H460, H1299, H441, H522, DAOY, D283, SKBR3, Jurkat, B 16F10, A549, MDA-MB-231, LNCaP, HCT116, or LLC cell line.

33. A method of inhibiting PFKFB4 in a subject, the method comprising administering to the subject an effective amount of the compound of claim 1,
    wherein (a) the subject has cancer and (b) the cancer is (i) acute lymphoblastic leukemia, astrocytoma, basal cell carcinoma, bladder cancer, brain cancer, brain tumors, breast cancer, chronic lymphocytic leukemia (CLL), colon cancer, colorectal cancer, diffuse large B-cell lymphoma, gastric cancer, glioblastoma, glioblastoma multiforme, glioma, hematological malignancies, leukemias, lung cancer, lymphoma, medulloblastoma, neuroblastoma, non-Hodgkin lymphoma, non-small cell lung cancer, pancreatic cancer, prostate cancer, and rectal cancer, (ii) metastatic cancers resulting from (i), or (iii) cancerous tumors of (i) or (ii).

34. The method of claim 33, wherein the compound is administered at a dosage effective for specifically inhibiting PFKFB4.

35. The method of claim 33, wherein the compound is administered orally or administered intravenously.

36. The method of claim 33, wherein the cancer is (i) non-small cell lung cancer, colorectal cancer, prostate cancer, breast cancer, pancreatic cancer, lymphoma, or medulloblastoma or (ii) cancerous tumors of (i).

37. The method of claim 33, wherein the canner is (i) non-small cell lung cancer, colorectal cancer, prostate cancer, or breast cancer or (ii) cancerous tumors of (i).

38. The method of claim 33, wherein the cancer is non-small cell lung cancer and cancerous tumors thereof.

39. The method of claim 33, wherein the method treats breast cancer or cancerous tumors thereof.

40. The method of claim 33, wherein the subject remains substantially free of signs of toxicity.

41. A method of reducing glycolytic flux in a cell, the method comprising contacting the cell with an effective amount of the compound of claim 1.

42. The method of claim 41, wherein the cell is a mammalian cell.

43. The method of claim 41, wherein the cell is a cancer cell.

44. The method of claim 41, wherein the cell is H460, H1299, H441, H522, DAOY, D283, SKBR3, Jurkat, B16F10, A549, MDA-MB-231, LNCaP, HCT116, or LLC cell line.

45. A method of reducing proliferative capacity of a cell, the method comprising contacting the cell with an effective amount of the compound of claim 1.

46. The method of claim 45, wherein the cell is contacted with the compound at a dosage effective for specifically inhibiting PFKFB4.

47. The method of claim 45, wherein the cell is a mammalian cell.

48. The method of claim 45, wherein the cell is a cancer cell.

49. The method of claim 45, wherein the cell is H460, H1299, H441, H522, DAOY, D283, SKBR3, Jurkat, B16F10, A549, MDA-MB-231, LNCaP, HCT116, or LLC cell line.

50. A method of reducing fructose-2,6-bisphosphate (F2, 6BP) in a cell, the method comprising contacting the cell with an effective amount of the compound of claim 1.

51. The method of claim 50, wherein the cell is a mammalian cell.

52. The method of claim 50, wherein the cell is a cancer cell.

53. A method for preparing a compound of claim 1, the method comprising,
  (a) reacting a compound of Formula (II) with a compound of Formula (III) to result in a mixture comprising a compound of Formula (IV);
  (b) reacting a compound of Formula (IV) with a compound of Formula (V); and;
  (c) recovering the compound of claim 1,
wherein Formula (II) is

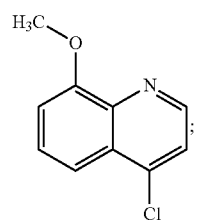

(II)

Formula (III) is

(III)

Formula (IV) is

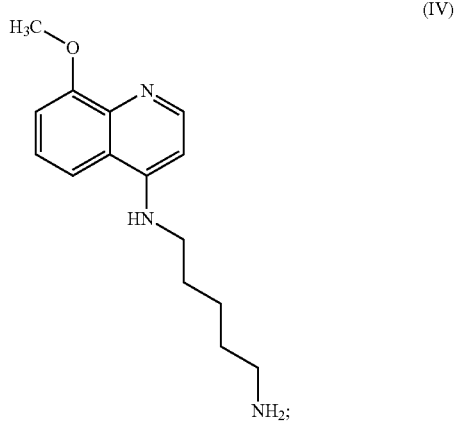 [SMILES: COc1cccc2c(NCCCCCN)ccnc12]

(IV)

and
Formula (V) is

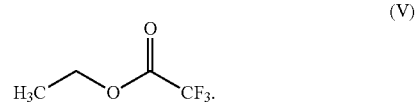

(V)

54. The method of claim 53, wherein the method is for preparing Formula (I).

55. The method of claim 17, wherein the method treats breast cancer or cancerous tumors thereof.

* * * * *